US009315776B2

(12) United States Patent
Fong et al.

(10) Patent No.: US 9,315,776 B2
(45) Date of Patent: Apr. 19, 2016

(54) WHARTON'S JELLY MESENCHYMAL STEM CELLS AND USES THEREOF

(71) Applicant: National University of Singapore, Singapore (SG)

(72) Inventors: Chui Yee Fong, Singapore (SG); Tuan Ariffeen Bongso, Singapore (SG); Arijit Biswas, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/667,370

(22) Filed: Nov. 2, 2012

(65) Prior Publication Data

US 2013/0302285 A1 Nov. 14, 2013

Related U.S. Application Data

(60) Provisional application No. 61/557,665, filed on Nov. 9, 2011.

(51) Int. Cl.
*C12N 5/0789* (2010.01)
*A61K 35/28* (2015.01)
*C12N 5/0775* (2010.01)

(52) U.S. Cl.
CPC .............. *C12N 5/0647* (2013.01); *A61K 35/28* (2013.01); *C12N 5/0668* (2013.01); *C12N 2502/1388* (2013.01)

(58) Field of Classification Search
None
See application file for complete search history.

(56) References Cited

U.S. PATENT DOCUMENTS

| 2004/0072259 | A1* | 4/2004 | Scadden et al. ................. 435/7.2 |
| 2007/0166825 | A1 | 7/2007 | Hatsuyama et al. |
| 2008/0118477 | A1* | 5/2008 | Christopherson ............ 424/93.7 |
| 2008/0220520 | A1 | 9/2008 | Palecek et al. |
| 2014/0120615 | A1 | 5/2014 | Fong et al. |

FOREIGN PATENT DOCUMENTS

| KR | 2010-0114729 A | 10/2010 |
| WO | WO 2006/036130 A1 | 4/2006 |
| WO | WO 2007/046775 A1 | 4/2007 |
| WO | WO 2008/060377 A2 | 5/2008 |
| WO | WO 2011/101760 A1 | 8/2011 |
| WO | WO 2011/120535 A1 | 10/2011 |
| WO | WO 2014/027965 A1 | 2/2014 |

OTHER PUBLICATIONS

Magin et al., Stem Cells and Development, vol. 18, No. 1, 2009,pp. 173-185.*
Irvine et al., Exp. Hematol. vol. 12, No. 1, 1984, pp. 19-24.*
Venugopal et al., Stem Cells and Cloning: Advances and Appications 2011: 4, pp. 39-50.*
Cardone. A., et al., "Prognoostic Value of Desmoplastic Reaction and Lyphocytic Infiltration in the Management of Breast Cancer", *Panminerva Med*, 39(3):174-177 (1997).
Guathaman, K., et al., "Osteogenic Differentiation of Human Wharton's Jelly Stem Cells on Nanofibrous Substrates in Vitro", *Tissue Engineering Part A*, 17 (1-2): 71-81 (2011).
Lemoli, R.M., et al., "Interleukin-11 Stimulates the Proliferation of Human Hematopoietic CD34+ and CD34+CD33−DR− Cells and Synergizes With Stem Cell Factor, Interleukin-3, and Granulocyte-Macrophage Colony-Stimulating Factor", *Exp Hematology*, 31: 1668-1672 (1993).
Pappa, K.I. and Anagnou, N.P., "Novel Sources of Fetal Stem Cells: Where Do They Fit on the Developmental Continuum?", *Regen Med*, 4(3): 423-433 (2009).
Pezzolesi, M.G., et al., "Mutation-Positive and Mutation-Negative Patients With Cowden and Bannayan-Riley-Ruvalcaba Syndromes Associated With Distinct 10q Haplotypes", *The American Journal of Human Genetics*, 79: 923-934 (2006).
Takzare, N., et al., "Influence of Aloe Vera Gel on Dermal Wound Healing Process in Rat", *Toxicology Mechanisms and Methods*, 19: 73-77 (2009).
Weiss, M.L., et al., "Immune Properties of Human Umbilical Cord Wharton's Jelly-Derived Cells", *Stem Cells*, 26:2865-2874 (2008).
Welch, W.J., et al., "Response of Mammalian Cells to Metabolic Stress; Changes in Cell Physiology and Structure/Function of Stress Proteins", *Curr Top Microbiol Immunol*, 167: 31-55 (1991).
Wexler, S.A., et al., "Adult Bone Marrow Is a Rich Source of Human Mesenchymal Stem Cells But Umbilical Cord and Mobilized Adult Blood Are Not", *British Journal of Haematology*, 121: 368-374 (2003).
Yew, T.L., et al., "Enhancement of Wound Healing by Human Multipotent Stromal Cell Conditioned Medium: the Paracrine Factors and p38 MAPK Activation", *Cell Transplantation*, 20: 693-706 (2011).
PCT/SG2013/000348,"Wo und Dressing Nanomesh Impregnated with Human Umbilical Cord Wharton's Jelly Stem Cells", Aug. 15, 2013, Chui Yee Fong, Mahesh Choolani, Arij it Biswas, Tuan Ariffeen Bongso and Seeram Ramakrishna.
U.S. Appl. No. 14/069,557, filed Nov. 1, 2013, Chui Yee Fong, Tuan Ariffeen Bongso and Daniel Hao Lin.
Azari, O., et al., "Effects of Transplanted Mesenchymal Stem Cells Isolated from Wharton's Jelly of Caprine Umbilical Cord on Cutaneous Wound Healing; Histopathological Evaluation", Vet Res Commun, 35(4): 211-222 (2011).

(Continued)

*Primary Examiner* — Thane Underdahl
*Assistant Examiner* — Yvonne Pyla
(74) *Attorney, Agent, or Firm* — Hamilton, Brook, Smith & Reynolds, P.C.

(57) ABSTRACT

In one aspect, the invention is directed to methods of expanding hematopoietic stem cells (HSCs) comprising culturing the HSCs with Wharton's Jelly mesenchymal stem cells (WJSCs), a cell culture medium that has been conditioned with WJSCs, or a combination thereof, thereby producing a HSC culture; and maintaining the HSC culture under conditions in which the HSCs expand in the culture, thereby expanding the HSCs. In another aspect, the invention is directed to a method of transplanting the expanded HSCs in an individual in need thereof. In yet another aspect, the invention is directed to compositions comprising HSCs and Wharton's Jelly mesenchymal stem cells (WJSCs). The composition can further comprise a cell culture medium that has been conditioned with WJSCs.

39 Claims, 14 Drawing Sheets

(56) References Cited

OTHER PUBLICATIONS

Cabrera, C., et al., "The Role of Biologically Active Peptides in Tissue Repair Using Umbilical Cord Mesenchymal Stem Cells", Ann N Y Acad Sci., 1270: 93-97 (2012).
Kim, J.Y., et al., "Human Cord Blood-Derived Endothelial Progenitor Cells and Their Conditioned Media Exhibit Therapeutic Equivalence for Diabetic Wound Healing", Cell Transplantation, 19: 1635-1644 (2010).
Manncllo, F., et al., Concise Review: No Breakthroughs for Human Mesenchymal and Embryonic Stem Cell Culture: Conditioned Medium, Feeder Layer, or Feeder-Free: Medium with Fetal Calf Serum, Human Serum, or Enriched Plasma; Serum-Free, Serum Replacement Nonconditioned Medium, or Ad Hoc Formula? All That Glitters Is Not Gold!, Stem Cells, 25: 1603-1609 (2007).
Shohara, R., et al., "Mesenchymal Stromal Cells of Human Umbilical Cord Wharton's Jelly Accelerate Wound Healing by Paracrine Mechanisms", Cytotherapy, 14(10): 1171-1181 (2012).
International Search Report and the Written Opnion of the International Searching Authority for International Patent Application No. PCT/SG2013/000348, "Wound Dressing Nanomesh Impregnated with Human Umbilical Cord Wharton's Jelly Stem Cells", date of mailing Oct. 22, 2013.
Notification Concerning Transmittal of International Preliminary Report on Patentability for International Patent Application No. PCT/SG2013/000348, "Wound Dressing Nanomesh Impregnated with Human Umbilical Cord Wharton's Jelly Stem Cells", date of mailing Feb. 26, 2015.
Applicant Initiated Interview Summary for U.S. Appl. No. 14/069,557, "Methods of Freezing Stem Cells"; date of mailing Aug. 10, 2015.
Non-Final Office Action for U.S. Appl. No. 14/069,557, "Methods of Freezing Stem Cells"; date of mailing May 8, 2015.
U.S. Appl. No. 14/421,676 entitled "Wound Dressing Nanomesh Impregnated With Human Umbilical Cord Wharton's Jelly Stem Cells" filed Aug. 15, 2013.
Akino, K., et al., "Human Mesenchymal Stem Cells May Be Involved In Keloid Pathogenesis", International Journal of Dermatology, 47(11): 1112-1117 (2008).
Al-Anazi, K., "Autologous Hematopoietic Stem Cell Transplantation For Multiple Myeloma Without Cryopreservation", Bone Marrow Research, Article ID 971361: 7 pages (2012).
Ayuzawa, R., et al., "Naïve Human Umbilical Cord Matrix Derived Stem Cells Significantly Attenuate Growth Of Human Breast Cancer Cells In Vitro and In Vivo", Cancer Letters, 280: 31-37 (2009).
Badiavas, E.V., et al., "Participation Of Bone Marrow Derived Cells In Cutaneous Wound Healing", Journal Of Cellular Physiology, 196: 245-250 (2003).
Badiavas, E.V. and Falanga, V., "Treatment of Chronic Wounds With Bone Marrow-Derived Cells", Arch Dertmatol, 139 510-516 (2003).
Baharvand, H., et al., "An Efficient And Easy-To-Use Cryopreservation Protocol For Human ES And iPS Cells", Nat Protoc, 5(3): 588-594 (2010).
Bakhshi, T., et al., "Mesenchymal Stem Cells From The Wharton's Jelly Of Umbilical Cord Segments Provide Stromal Support For The Maintenance Of Cord Blood Hematopoietic Stem Cells During Long-Term Ex Vivo Culture", Transfusion, 48(12): 2638-2644 (2008).
Bao, P., et al., "The Role Of Vascular Endothelial Growth Factor In Wound Healing", J Surg Res, 153(2): 347-358 (2009).
Berz, D., et al., "Cryopreservation Of Hemaotpoietic Stem Cells", American Journal of Hematology, 82: 463-472 (2007).
Bey, E., et al., "Emerging Therapy For Improving Wound Repair Of Severe Radiaiton Burns Using Local Bone Marro-Derived Stem Cell Administrations", Wound Repair and Regeneration, 18:50-58 (2010).
Bielefeld, K.A., et al., "Fibronectin And β-Catenin Act In A Regulatory Loop In Dermal Fibroblasts To Modulate Cutaneous Healing", J Biol Chem, 286(31): 27687-27697 (2011).
Bissel, M.J. and RAdisky, D., "Putting Tumours In Context", Nat Rev Cancer, 1(1): 45-54 (2001).

Blankenstein, T., "The Role Of Tumor Stroma In The Interaction Between Tumor And Immune System", Current Opinion in Immunology, 17: 180-186 (2005).
Blit, P.H. and Jeschke, M.G., "Keloids: Whe Do We Know And What Do We Do Next?", Transl Res, 159(3): 173-174 (2012).
Bongso, A. and Fong, C.Y., "The Therapeutic Potential, Challenges And Future Clinical Directions Of Stem Cells From Wharton's Jelly Of The Human Umbilical Cord", Stem Cell Rev, 9(2): 226-240 (2013).
Borue, X., et al., "Bone Marrow-Derived Cells Contribute To Epithelial Engraftment During Wound Healing", American Journal of Pathology, 165(5): 1767-1772 (2004).
Brower, J., et al., "Mesenchymal Stem Cell Therapy And Delivery Systems In Nonhealing Wounds", Advances in Skin & Wound Care, 24:524-532 (2011).
Broxmeyer, H.E., "Insights Into The Biology Of Cord Blood Stem/Progenitor Cells", Cell Proliferation, 44: 55-59 (2010).
Bueno, C., et al., The ROCK Inhibitor Y-27632 Negatively Affects The Expansion /Survival Of Both Fresh And Cryopreserved Cord Blood-Derived CD34+ Hematopoietic Progenitor Cells, Stem Cell Rev and Rep, 6: 215-223 (2010).
Chao, K.C., et al., "Islet-Like Clusters Derived From Mesenchymal Stem Cells In Wharton's Jelly Of The Human Umbilical Cord For Transplantation To Control Type I Diabetes" PlosOne, e1451: 9 pages (2008).
Chao, K.C., et al., "Human Umbilical Cord MEsenchymal Stem Cells Suppress Breast Cancer Tumourigenesis Through Direct Cell-Cell Contact And Internalization", J. Cell Mol Med, 16(8): 1803-1815 (2012).
Chen, L., et al., "Analysis of Allogenicity Of Mesenchymal Stem Cells In Engraftment and Wound Healing In Mice", Plos One, e7119, 4(9): 7 pages (2009).
Chithra, P., et al., "Influence Of Aloe Vera On Collagen Characteristics In HEaling Dermal Wounds In Rats", Molecular and Cellular Biochemistry 181: 71-76 (1998).
Chithra, P., et al., "Influence Of Aloe Vera On The Healing Of Dermal Wounds In Diabetic Rats", J Ethnopharmacol, 56(3): 195-201 (1998).
Clark, R.A.F., Fibronectin Matrix Depostion And Firbonectin Receptor Expression In Healing And Normal Skin, J Invest Dermatol, 94: 128S-134S (1990).
Clarke, D.M., et al., "Improved Post-Thaw Recovery Of Peripheral Blood Stem/Progenitor Cells Using A Novel Intracellular-Like Cryopreservation Solution", Cytotherapy, 11(4): 472-479 (2009).
Cory, G., "Scratch-Wound Assay", Methods Mol Biol, 769: 25-30 (2011).
de Boer, F., et al., "Extensive Early Apoptosis In Frozen-Thawed CD24-positive Stem Cells Decreases Threshold Doses For Haematological Recovery After Autologous Peripheral Blood Progenitor Cell Transplantation", Bone Marrow Transplantation, 29: 249-255 (2002).
de Boer, F., et al., "Early Apoptosis Largely Accounts For Functional Impairment Of CD34+ Cells In Frozen-Thawed Stem Cell Grafts", J Hematother Stem Cell Res, 11(6): 951-963 (2002).
Dominici, M., et al., "Minimal Criteria For Defining Multipotent Mesenchymal Stromal Cells. The International Society For Cellular Therapy Position Statement", Cytotherapy, 8(4): 315-317 (2006).
Durand, E.M. And Zon, L.I., "Newley Emerging Roles For Prostaglandin $E_2$ Regulation Of Hematopoiesis And Hematopoietic Stem Cell Engraftment", Current Opinion In Hematology, 17: 308-312 (2010).
Ehrlich, H.P., et al., "Morphological And Immunochemical Differences Between Keloid And Hypertrophic Scar", American Journal Of Pathology, 145(1): 105-113 (1994).
Estes, J.M., et al., "Hyaluronate Metabolism Undergoes An Ontogenic Transiton During Fetal Development: Implications For Scar-Free Wound Healing", J. Pediatr Surg, 28(10): 1227-1231 (1993).
Fan, C.G., et al., "Therpeutic Potentials Of Mesenchymal Stem Cells Derived From Human Umbilical Cord", Stem Cell Rev and Rep, 7(1): 195-207 (2011).

(56) References Cited

OTHER PUBLICATIONS

Fathke, C., et al., "Contribution Of Bone Marrow-Derived Cells To Skin: Collagen Depostion And Wound Repair", *Stem Cells*, 22: 812-822 (2004).

Fernandes, K.J.L., et al., "A Dermal Niche For Multipotent Adult Skin-Derived Precursor Cells", Nature Cell Biology, 6(11):1082-1093 plus 5 pages of Supplemental Information (2004).

Fleming, K.K. and Hubel, A., "Cryopreservation Of Hematopoietic STem Cells: Emerging Science, Technology and Issues", Transfusion Medicine and Hemotherapy, 34: 268-275 (2007).

Fong, C.Y., et al., "Comparative Growth Behaviour And Characterization Of Stem Cells From Human Wharton's Jelly", *Reproductive BioMedicine Online*, 15(6): 708-718 (2007).

Fong, C.Y., et al., "Derivation Efficiency, Cell Proliferation, Freeze-Thaw Survival, Stem-Cell Properties And Differentiation Of Human Warton's Jelly Stem Cells", *Reproductive BioMedicine Online*, 21: 391-401 (2010).

Fong, C.Y., et al., "Human Wharton's Jelly Stem Cells Have Unique Transciptome Profiles Compared To Human Embryonic Stem Cells And Other Mesenchymal Stem Cells", Stem Cell Rev, 7(1): 1-16 (2011).

Fong, C.Y., et al., "Human Umbilical Cord Wharton's Jelly Stem Cells And Its Conditioned Medium Support Hematopoietic Stem Cell Expansion Ex Vivo", *J of Cellular Biochemistry*, 113: 658-668 (2012).

Fong, C.Y., et al., "Human Umbilical Cord Wharton's Jelly Stem Cells Undergo Enhanced Chondrogenic Differentiation When Grown On Nanofibrous Scaffolds And In A Sequenctial Two-Stage Culture Medium Environment", Stem Cell Rev and Rep, 8: 195-209 (2012).

Fonseka, M., et al., "Human Umbilical Cord Blood-Derived Mesenchymal Stem Cells (hUCB-MSC) Inhibit The Proliferation of K562 (Human Erythromyeloblastoid Leukaemic Cell Line)", Cell Biol Int, 36: 793-801 (2012).

Ganta, C., et al., "Rat Umbilical Cord Stem Cells Completely Abolish Rat Mammary Carcinomas With No Evidence Of Metastasis Or Recurrence 100 Days Post-Tumor Cell Inoculation", Cancer Res, 69(5): 1815-1820 (2009).

Garin, M.I., et al., "Ex Vivo Expansion And Charachtersation Of CD34+ Cells Derived From Chronic Myeloid Leukaemia Bone Marrow And Peripheral Blood, And From Normal Bone Marrow And Mobilised Peripheral Blood", Eur J Haematol, 64(2): 85-92 (2000).

Gauglitz, G.G., et al., "Hypertrophic Scarring And Keloids: Pathomechanisms And Current And Emerging Treatment Strategies", Mol Med, 17: 113-125 (2011).

Gauglitz, G.G., "Management Of Keloids And Hypertrophic Scars: Current And Emerging Options", Clinical, Cosmetic and Investigational Dermatology, 6: 103-114 (2013).

Gauthaman, K., et al., "ROCK, Inhibitor Y-27632 Increase Thaw-Survival Rates And Preserves Stemness And Differentiation Potential Of Human Wharton's Jelly Stem Cells After Cryopreservation", Stem Cell Rev and Rep, 6(4): 665-676 (2010).

Gauthaman, K., et al., "Extra-Embryonic Human Wharton's Jelly Stem Cells Do Not Induce Tumorigenesis, Unlike Human Embryonic Stem Cells", *Reproductive BioMedicine Online*, 24: 235-246 (2012).

Gauthaman, K., et al, "Human Umbilical Cord Wharton's Jelly Stem Cell (hWJSC) Extracts Inhibit Cancer Cell Growth In Vitro", *J Cell Biochem*, 113(6): 2027-2039 (2012).

Gauthaman, K., et al, "Human Wharton's Jelly Stem Cell Conditioned Medium And Cell-Free Lysate Inhibit Human Osteosarcoma And Mammary Carcinoma Cell Growth In Vitro And In Xenograft Mice", J Cell Biochem, 114(2): 366-377 (2013).

Gay, A.N., et al., "Wound Healing Characteristics of ICAM-1 Null Mice Devoid Of All Isoforms Of ICAM-1", *J Surg. Res*, 171(1): e1-e7 (2011).

Gluckman, E., et al., "Outcome Of cord-Blood Transplantation From Related And Unrelated Donors", NEJM, 337(6): 373-381 (1997).

Gluckman, E., et al., "Cord Blodd Transplantation: State Of The Art", Haematologica, 94(4): 451-454 (2009).

Hana, J. and Hubel, A., "Preservation Of Stem Cells", Organogenesis, 5(3): 134-137 (2009).

Harris, D.T., et al., "Cell-Based Therapy For Epithelial Wounds", Cytotherapy, 14(7): 802-810 (2012).

Hayakawa, J., et al., "5% Dimethyl Sulfoxide (DMSO) And Pentastarch Improves Cryopreservation Of Cord Blood Cells Over 10% DMSO", *Transfusion*, 50(10): 2158-2166 (2010).

Hoggatt, J., et al., "Prostaglandin $E_2$ Enhances Hematopoietic Stem Cell Homing, Survival, And Proliferation", Blood, 113(22): 5444-5455 (2009).

Huang, Y.C., et al., "Umbilical Cord Versus Bone Marrow-Derived Mesenchymal Stromal Cells", Stem Cells And Development, 21(15): 2900-2903 (2012).

Iqbal, S.A., et al., "Identification Of Fibrocytes From Mesenchymal Stem Cells In Keloid Tissue: A Potential Source Of Abnormal Fibroblasts In Keloid Scarring", Arch Dermatol Res, 304(8): 665-671 (2012).

Hamann, K.J., et al., "Hyaluronic Acid Enhances Cell Proliferation During Eosinopoiesis Through The CD44 Surface Antigen", J Immunol, 154(8): 4073-4080 (1995).

Heng, B.C., "Effect Of Rho-Associated Kinase (ROCK) Inhibitor Y-27632 On The Post-Thaw Viability Of Cryopreserved Human Bone Marrow-Derived Mesenchymal Stem Cells", Tissue Cell, 41(5): 376-380 (2009).

Jackson, W.M., et al., "Concise Review: Clinical Translation Of Wound Healing Therapies Based On Mesenchymal Stem Cells", Stem Cells Translational Medicine, 1: 44-50 (2012).

Jäger, R. and Fearnhead, H.O., "'Dead Cells Talking': The Silent Form Of Cell Death Is Not So Quiet", *Biochemistry Research International*, Article ID 453838: 8 pages (2012).

Jeon, Y.K., et al., "Mesenchymal Stem Cells' Interaction With Skin: Wound-Healing Effect On Fibroblast Cells And Skin Tissue: *Wound Repair Regen*, 18(6): 655-661 (2010).

Ji, R., et al., "MicroRNA Expression Signature And Antisense-Mediated Depletion Reveal An Essential Role Of MicroRNA In VAscular Neointimal Lesion Formation", *Circ Res*, 100: 1579-1588 (2007).

Jin, G., et al., "Stem Cell Differentiation To Epidermal Lineages On Electrospun Nanofibrous Substrates For Skin Tissue Engineering", Acta Biomater, 7(8): 3113-3122 (2011).

Jodele, S., et al., "The Contribution Of Bone Marrow-Derived Cells To The Tumor Vasculature In Neuroblastoma Is Matrix Metalloproteinase-9 Dependent" Cancer Res, 65(8): 3200-3208 (2005).

Karahuseyinoglu, S., et al., "Biology Of Stem Cells In Human Umbilical Cord Stroma: In Situ And In Vitro Surveys", *Stem Cells*, 25: 319-331 (2007).

Karolina, D.S., et al., "MicroRNA 144 Impairs Insulin Signaling By Inhibiting The Expression Of Insulin Receptor Substrate 1 In Type 2 Diabetes Mellitus", *Plos One*, e22839, 6(8): 19 pages (2011).

Kawachi, Y., et al., "Superficial Epithelioma With Sebaceous Differentiation: Immunohistochemical Study Of Keratinocyte Differentiation Markers", *Eur J Dermatol*, 21(6): 1016-1017 (2011).

Kieran, I., et al., "Interleukin-10 Reduces Scar Formation In Both Animal And Human Cutaneous Wounds: REsults Of Two Preclinical And Phase II Randomized Control Studies", Wound Repair Regen 21(3): 428-436 (2013).

Krishnan, A. and Forman, S.J., "Hematopoietic STem Cell Transplantation for AIDS Related Malignancies", Curr Opin Oncol, 22(5): 456-460 (2010).

Kuo, Y.R., et al., "Bone Marrow-Derived Mesenchymal Stem Cells Enhanced Diabetic Wound Healing Through Recruitment Of Tissue Regeneration In A Rat Model Of Streptozotocin-Induced Diabetes", Plas. Reconstr Surg 128: 872-880 (2011).

Kuzuya, H., et al., "Determination Of Aloenin, Barbaloin And Isobarbaloin In Aloe Species By Micellar Electrokinetic Chromatography", J Chromatogr B Biomed Sci Appl, 572: 91-97 (2001).

LaRocca, G., et al., "Isolation And Characterization Of Oct-4+/HLA-G+ Mesenchymal Stem Cells From Human Umbilical Cord Matrix: Differntiation Potential And Detection Of New Markers", Histochem Cell Biol, 131(2): 267-282 (2009).

Li, F., et al., "Apoptotic Cells Activate The "Phoenix Rising" Pathway to Promote Wound Healing And Tissue Regeneration", *Sci Signal*, ra 13, 3(110): 20 pages (2010).

(56) References Cited

OTHER PUBLICATIONS

Liang, C.C., et al., "In Vitro Scratch Assay: A Convenient And Inexpensive Method For Analysis Of Cell Migration In Vitro", *Nature Protocols*, 2(2): 329-333 (2007).
Liao, B., et al., "MicroRNA Cluster 302-367 Enhances Somatic Cell Reprogramming By Accelerating A Mesenchymal-To-Epithelial Transition", *The Journal of Biological Chemistry*, 286(19): 17359-17364 (2011).
Limaye, L.S. and Kale, V.P., "Cryopreservation Of Human Hematopoietic Cells With Membrane Stabilizers And Bioantioxidants As Additives In The Conventional Freezing Medium", J Hematother Stem Cell Res, 10(5): 709-718 (2001).
Liu, C., et al., "A Novel PTEN Gene Promoter Mutation And Untypical Cowden Syndrome", Clin J Cancer Res, 25(3): 306-311 (2013).
Liu, J., et al., "Suppression Of Cholangiocarcinoma Cell Growth By Human Umbilical Cord Mesenchymal Stem Cells: A Possible Rold of Wnt and Akt Signaling", PlosOne, 8(4): e62844, 11 pages (2013).
Liu, Y., et al., "Increased Matrix Metalloproteinase-9 Predicts Poor Wound Healing In Diabetic Foot Ulcers", *Diabetes Care*, 32(1): 117-119 (2009).
Lorenz, H.P., et al, "Scarless Wound Repair: A Human Fetal Skin Model", Development, 114: 253-259 (1992).
Luo, G., et al., "Promotion Of Cutaneous Wound Healing By Local Application Of Mesenchymal Stem Cells Derived From Human Umbilical Cord Blood", Wound Repair Regen, 18(5): 506-513 (2010).
Ma, K., et al., "Effects Of Nanofiber/Stem Cell Composite On Wound Healing In Acute Full-Thickness Skin Wounds," Tissue Eng Part A, 17(9-10): 1412-1424 (2011).
Ma, Y., et al., "The In Vitro And In Vivo Effects Of Human Umbilical Cord Mesenchymal Stem Cells On The Growth Of Breast Cancer Cells", Breast Cancer Res Treat, 133(2): 473-485 (2012).
Madhyastha, R., et al., "MicroRNA Signature In Diabetic Wound Healing: Promotive Role of miR-21 In Fibroblast Migration", *Int Wound J*, 9(4): 355-361 (2012).
MaHam, A., et al., "Protein-Based Nanomedicine Platforms For Drug Delivery", Small, 5(15): 1706-1721 (2009).
Mansilla, E., et al., "Human Mesenchymal Stem Cells ARe Tolerized By Mice And Improve Skin And Spinal Cord Injuries", Transplant Proc, 37(1): 292-294 (2005).
Mareschi, K., et al., "Isolation Of Human Mesenchymal Stem Cell: Bone Marrow Versus Umbilical Cord Blood", Haematologica, 86: 1099-1100 (2001).
Martin, P., et al., "Wound Healing In The PU.1 Null Mouse-Tissue Repair Is Not Dependent On Inflammatory Cells", Current Biology, 13: 1122-1128 (2003).
Maurya, D.K., et al., "Therapy With Un-Engineered Naïve Rat Umbilical Cord Matrix Stem Cells Markedly Inhibits Growth Of Muring Lung Adenocarcinoma", BMC Cancer, 10: 10 pages (2010).
Maxson, S., et al., "Concise Review: Role Of Mesenchymal Stem Cells In Wound Repair", Stem Cells Translational Medicine, 1: 142-149 (2012).
Mendonça, F.A.S., et al., "Effects Of The Application Of Aloe Vera (1.) And Microcurrent On The Healing Of Wounds Surgically Induced In Wistar Rats", Acta Cir Brasileira, 24(2): 150-155 (2009).
Mogili, N.S., et al., "Altered Angiogenic Balance In Keloids: A Key To Therpeutic Intervetion", Transl Res, 159(3): 182-189 (2012).
Moon, J.H., et al., "Isolation And Characterization Of Multipotent Human Keloid-Derived Mesenchymal-Like Stem Cells", Stem Cells Dev 17(4): 713-724 (2008).
Moshref, S.S. and Mufti, S.T., "Keloid And Hypertrophic Scars: Comparative Histopathological And Immunohistochemical Study", *JKAU: Med. Sci.*, 17(3): 3-22 (2010).
Muller, M., et al., "Matrix Metalloproteinases And Diabetic Foot Ulcers: The Ratio Of MMP-1 to TIMP-1 Is A Predictor Of Wound Healing", *Diabetic Med*, 25: 419-426 (2008).
Murphy, G. and Nagase, H., "Progress In Matrix Metalloproteinase Research", Mol. Aspects Med, 29(5): 290-308 (2008).
Musina, R.A., et al., "Umbilical Cord Blood Mesenchymal Stem Cells", *Bull Exp Biol Med*, 143(1): 127-131 (2007).
Nagaoka, T., et al., "Delayed Wound Healing In The Absence Of Intracellular Adhesion Molecule-1 or L-Selectin Expression", *American Journal Of Pathology*, 157(1): 237-247 (2000).
Nekanti, U., et al., "Lone-Term Expansion And Pluripotent Marker Array Analysis Of Wharton's Jelly-Derived Mesenchymal Stem Cells", Stem Cell Dev, 19(1): 117-130 (2010).
Pastrana, E., et al., "Eyes Wide Open: A Critical Review Of Sphere-Formation As An Assay For Stem Cells", Cell Stem Cell, 8(5): 486-498 (2011).
Prasanna, S.J. and Jahnavi, V.S., "Wharton's Jelly Mesenchymal Stem Cells As Off-The-Shelf Cellular Therapeutics: A Closer Look Into Their Regenerative And Immunomodulatory Properties", The Open Tissue Engineering And Regenerative Medicine Journal, 4: 28-38 (2011).
Rachakatla, R.S., et al., "Development Of Human Umbilical Cord Matrix Stem Cell-Based Gene Therapy For Experimental Lung Tumors", Cancer Gene Therapy, 14: 828-835 (2007).
Rebulla, P., "Cord Blood Banking 2002: 112,010 Of 7,914,773 Chances", Transfusion, 42(10): 1246-1248 (2002).
Robinson, S.N., et al., "Mesenchymal Stem Cells In Ex Vivo Cord Blood Expansion", Best Pract Res Clin Haematol, 24: 83-92 (2011).
Romanov, Y.A., et al., "Searching For Alternative Sources Of Postnatal Human Mesenchymal Stem Cells: Candidate MSC-Like Cells From Umbilical Cord", *Stem Cells*, 21: 105-110 (2003).
Rnjak, J., et al., "Severe Burn Injuries And The Role Of Elastin In The Design Of Dermal Substitutes", *Tissue Eng Part B Rev*, 17(2): 81-91 (2011).
Salama, H., et al., "Autologuous Hematopoietic Stem Cell Transplantation In 48 Patients With End-Stage Chronic Liver Disease", Cell Transplantation, 16: 1475-1486 (2010).
Sarugaser, R., et al., "Human Umbilical Cord Perivascular (HUCPV) Cells: A Source Of Mesenchymal Progenitors", *Stem Cells* 23: 220-229 (2005).
Sasaki, M., et al, "Mesenchymal Stem Cells Are Recruited Into Wounded Skin And Contribute To Wound Repair By Transdifferentiation Into Multiple Skin Cell Type", The Journal of Immunology, 180: 2581-2587 (2008).
Sasnoor, L.M., et al., "Supplementation Of Conventional Freezing Medium With A Combination Of Catalase And Trehalose Results In Better Protection Of Surface Molecules And Functionality Of Hematopoietic Cells", J. Hematother Stem Cell Res, 12:553-564 (2003).
Sasnoor, L.M., et al., "A Combination Of Catalase And Trehalose As Additives To Conventional Freezing Medium Results In Improved Cryoprotection Of Human Hematopoietic Cells With REference To In Vitro Migration And Adhesion Properties", Transfusion, 45(4): 622-633 (2005).
Sasnoor, L.M., et al., "Prevention Of Apoptosis As A Possible Mechanism Behind Improved Cryoprotection Of Hematopoietic Cells by Catalase and Trehalose", Transplantation, 80: 1251-1260 (2005).
Schneider, R.K., et al., "Long-Term Survival And Characterisation Of Human Umbilical Cord-Derived Mesenchymal Stem Cells on Dermal Equivalents", Differentiation, 79(3): 182-193 (2010).
Seshareddy, K., et al., "Method To Isolate Mesenchymal-Like Cells From Wharton's Jelly Of Umbilical Cord", Method Cell Biol, 86: 101-119 (2008).
Shaw, T.J. and Martin, P., "Wound Repair At A Glance", Journal of Cell Science, 122(18): 3209-3213 (2009).
Shilo, S., et al., "Cutaneous Wound Healing AFter TReatment With Plant-Derived Human Recombinant Collagen Flowable Gel", Tiss Eng Part A, 19(13-14): 1519-1526 (2013).
Shin, L. and Peterseon, D.A., "Human Mesenchymal Stem Cell Grafts Enhance Normal And Impaired Wound Healing By Recruiting Existing Endogenous Tissue Stem/Progenitor Cells", Stem Cells Translational Medicine, 2: 33-42 (2013).
Spaeth, E.L., et al., "Mesenchymal Stem Cell Transition to Tumor-Associated Fibroblasts Contributes to Fibrovascular Network Expansion And Tumor Progression", PlosOne, 4(4): e4992: 11 pages (2009).
Stevens, L.J. and Page-McCaw, A., "A Secreted MMP Is Required For Reepithelialization During Wound Healing", *Molecular Biology Of The Cell*, 23: 1068-1079 (2012).

(56) References Cited

OTHER PUBLICATIONS

Stoff, A., et al., "Promotion Of Incisional Wound Repair By Human Mesenchymal Stem Cell Transplantation", Exp. Dermatol 18(4): 362-369 (2009).
Stroh, C., et al., "The Role Of Caspases In Cryoinjury: Caspase Inhibition Strongly Improves The Recovery Of Cryopreserved Hematopoietic And Other Cells", The FASEB Journal, 16: 1651-1653 (2002).
Suárez, Y., et al., "Dicer-Dependent Endothelial MicroRNAs Are Necessary For Postnatal Angiogenesis", *PNAS*, 105(37): 14082-14087 (2008).
Subramanian, A., et al., "Human Umbilical Cord Wharton's Jelly Mesenchymal Stem Cells Do Not Transform To Tumor-Associated Fibroblasts In The Presence Of Breast And Ovarian Cancer Cells Unlike Bone Marrow Mesenchymal Stem Cells", *J Cell Biochem*, 113(6): 1886-1895 (2012).
Sudo, K., et al, "Mesenchymal Progenitors Able To Differentiate Into Osteogenic, Chondrogenic, And/Or Adipogenic Cells In Vitro Are Present In Most Primary Fibroblast-Like Cell Populations", Stem Cells, 25: 1610-1617 (2007).
Sullivan, S.R., et al., "Validation Of A Model For The Study Of Multiple Wounds In The Diabetic Mouse (db/db)", *Plast Reconstr Surg*, 113(3): 953-960 (2004).
Sun, B., et al., "Human Umbilical Cord Blood Mesenchymal Stem Cell-Derived Extracellular Matrix Prohibits Metastic Cancer Cell MDA-MB-231 Proliferation", Cancer Lett, 196(2): 178-185 (2010).
Szulgit, G., et al., "Alterations In Fibroblast $\alpha 1 \beta 1$ Integrin Collagen Receptor Expression In Keloids And Hypertrophic Scars", Journal of Investigative Dermatology, 118: 409-415 (2002).
Taghizadeh, R.R., et al., "Wharton's Jelly Stern Cells: Future Clinical Applications", Placenta, 32: S311-S315 (2011).
Tocco, I., et al., "Nanotechnology-Based Therapies For Skin Wound Regeneration", Journal of Nanomaterials, Article ID 714134: 11 Pages (2012).
Toma, J.G., et al., "Isolation Of Multipotent Adult Stem Cells From The Dermis of Mammalian Skin", Nature Cell Biology, 3: 778-784 (2001).
Toma, J.G., et al., "Isolation and characterization Of Multipotent Skin-Derived Precursors From Human Skin", Stem Cells, 23: 727-737 (2005).
Troyer, D.L. and Weiss, M.L., "Concise Review: Wharton's Jelly-Derived Cells Are A Primitive STromal Cell Population", Stem Cells, 26: 591-599 (2008).
Vazquez, B., et al., "Antiinflammatory Activity Of Extracts From Aloe Vera Gel", J. Ethnopharmacol, 55: 69-75 (1996).
Walter, M.N., et al., "Mesenchymal Stem Cell-Conditioned Medium Accelerates Skin Wound Healing: An Invitro Study Of Fibroblast And Keratinocyte Scratch Assays", *Exp Cell Res*, 316(7): 1271-1281 (2010).
Wang, H.S., et al., "Mesenchymal Stem Cells In The Wharton's Jelly Of The Human Umbilical Cord", *Stem Cells*, 22: 1330-1337 (2004).
Wang, X.Y., et al., "Identificatin Of Mesenchymal Stem Cells In Aorta-Gonad-Mesonephros and Yolk Sac Of Human Embryos", Blood, 111(4): 2436-2443 (2008).
Wang, Y., et al., "A Toxicity Study Of Multiple-Administration Human Umbilical Cord Mesenchymal Stem Cells In Cynomolgus Monkeys", Stem Cells And Development, 21(9): 1401-1408 (2012).
Weiss, M.L., et al., "Human Umbilical Cord Matrix Stem Cells: Preliminary Characterization And Effect Of Transplantation In A Rodent Model Of Parkinson's Disease", *Stem Cells*, 24: 781-792 (2006).
Wels, J., et al, "Migratory Neighbors And Distant Invaders: Tumor-Associated Niche Cells", Genes & Development, 22:559-574 (2008).
White-Chu, E.F., et al., "Pressure Ulcers in Long-Term Care", Clin Geriatr Med, 17(2): 241-258 (2011).
Wu, S., et al., "Microvesicles Derived From Human Umbilical Cord Wharton's Jelly Mesenchymal Stem Cells Attenuate Bladder Tumor Cell Growth In Vitro And In Vivo", PlosOne, 8(4): e61366: 12 pages (2013).
Wu, Y., et al., "Mesenchymal Stem Cells Enhance Wound Healing Through Differentiation And Angiogenesis", *Stem Cells*, 25: 2648-2659 (2007).
Yang, F., et al., "Genetic Engineering Of Human Stem Cells For Enhanced Angiogenesis Using Biodegradable Polymeric Nanoparticles", PNAS, 107(8): 3317-3322 (2010).
Yukami, T., et al., "Endothelial Selectins Regulate Skin Wound Healing In Cooperation With L-Selectin And ICAM-1", *Journal Of Leukocyte Biology*, 82:519-531 (2007).
Zhang, K., et al., "Increased Types I and III Collagen And Transforming Growth Factor-$\beta 1$ mRNA And Protein In Hypertrophic Burn Scar", *J Invest Dermatol*, 104: 750-754 (1995).
Zhang, Q., et al., "Tumor-Like Stem Cells Derived From Human Keloid Are Governed By The Inflammatory Niche Driven By IL-17/IL-6 Axis", PlosOne, 4(11): e7798: 16 pages. (2009).
Zhang, Y., et al., "Co-Culture Of Umbilical Cord Blood CD34+ Cells With Human Mesenchymal Stem Cells", Tissue Engineering, 12(8): 2161-2170 (2006).
Zhang, Y.Z., et al., "Biomimetic and Bioactive Nanofibruous Scaffolds From Electrospun Composite Nanofibers", *International Journal Of Nanomedicine*, 2(4): 623-638 (2007).

\* cited by examiner

WHARTON'S JELLY MESENCHYMAL STEM CELLS AND USES THEREOF

RELATED APPLICATION

This application claims the benefit of U.S. Provisional Application No. 61/557,665, filed on Nov. 9, 2011.

The entire teachings of the above application(s) are incorporated herein by reference.

BACKGROUND OF THE INVENTION

Bone marrow hematopoietic stem cell (HSC) transplantation has been used for the treatment of malignant hematopoietic diseases. However, the aspiration of HSCs from the bone marrow is painful with the potential risk of infection and morbidity, and optimal HSC numbers are not always available for successful transplantation in many cases. To avoid these disadvantages, HSCs from the human umbilical cord blood (UCB) have been successfully used for the treatment of both malignant and non-malignant hematopoietic diseases in children in autologous and allogeneic settings. UCB contains HSCs and hematopoietic progenitor cells (HPCs) that appear to have higher proliferation rates and immunological tolerance compared to those in bone marrow. Unfortunately, UCB also has its limitations in that the HSC and HPC yields can be low and the cell numbers adequate for the treatment of hematopoietic diseases in children but not adults. It is estimated that for successful engraftment, at least $2.5 \times 10^6$ $CD34^+$ cells per kg of patient body weight is required but a good UCB harvest from a single umbilical cord generates only about $10 \times 10^6$ $CD34^+$ cells which is adequate for only a 4 kg child.

Several approaches have been suggested to alleviate the problems of inadequacy of HSC numbers for transplantation. These include (a) administration of a second UCB unit to the patient from another donor or (b) ex vivo expansion of the same patient's UCBHSCs. The latter approach is more favorable for immunological reasons as cell rejection can be avoided when autologous HSCs are administered. However, any expansion protocol must attempt to simulate as close as possible in vivo hematopoiesis while maintaining the stemness properties of the HSCs.

Human mesenchymal stem cells (MSCs) have been successfully used in vitro as a scaffold for stromal support and expansion of HSCs via cell-to-cell contact. This concept was developed based on the understanding that MSCs exist within the bone marrow in vivo and act as a natural scaffold on which the in vivo HSCs interact and proliferate. It is not definitely known whether the mechanism behind the HSC-MSC interaction that results in HSC proliferation is mediated by diffusible factors crossing over from the MSCs to HSCs during cell-to-cell contact or through secretions by the MSCs into the immediate microenvironment of the HSCs. To avoid immunological complications, autologous MSCs from the same patient's bone marrow or UCB have been used as a scaffold in vitro, for expansion of her own HSCs with successful results. However, the use of MSCs from UCB for stromal support of autologous HSCs has its own limitations in that the numbers of MSCs in UCB are extremely low and their existence in UCB has been controversial. Musina et al., (*Bull Exp Biol Med*, 143:127-131 (2007)) reported very low counts of UCB MSCs per volume of UCB and showed that such MSCs had low proliferation rates.

Thus, a need exists for improved methods of obtaining HSCs.

SUMMARY OF THE INVENTION

Shown herein is that umbilical cord Wharton's jelly serves as an attractive source of mesenchymal stem cells (MSCs), referred to herein as Wharton's jelly stem cells (WJSCs), for stromal coculture support for the expansion of hematopoietic stem cells (HSCs) when compared to other MSC sources. Also shown herein is that the conditioned medium (CM) of cultured WJSCs (referred to herein as WJSCCM), which contains a variety of beneficial growth factors secreted by the WJSCs such as interleukins and growth factors, provides good support for HSC expansion and its use likely requires less stringent approval from regulatory bodies for clinical application.

Accordingly, in one aspect, the invention is directed to methods of expanding hematopoietic stem cells (HSCs) comprising culturing the HSCs with Wharton's Jelly mesenchymal stem cells (WJSCs), a cell culture medium that has been conditioned with WJSCs, or a combination thereof, thereby producing a HSC culture; and maintaining the HSC culture under conditions in which the HSCs expand in the culture, thereby expanding the HSCs.

In another aspect, the invention is directed to a method of transplanting HSCs in an individual in need thereof comprising expanding (proliferating, growing) hematopoietic stem cells (HSCs) ex vivo comprising culturing (contacting, combining) the HSCs with Wharton's Jelly mesenchymal stem cells (WJSCs), a cell culture medium that has been conditioned with WJSCs, or a combination thereof, thereby producing a HSC culture. The HSC culture is maintained under conditions in which the HSCs expand in the culture, thereby expanding the HSCs and producing expanded HSCs. The expanded HSCs are introduced into the individual in need thereof, thereby transplanting HSCs in the individual. The expanded HSCs can be the individual's own HSCs that were expanded ex vivo using the methods provided herein.

In another aspect, the invention is directed to compositions comprising HSCs and Wharton's Jelly mesenchymal stem cells (WJSCs). The composition can further comprise a cell culture medium that has been conditioned with WJSCs.

In a particular aspect, the composition comprises hematopoietic stem cells (HSCs) and a cell culture medium that has been conditioned with Wharton's Jelly mesenchymal stem cells (WJSCs).

[Basal conditioned medium (BCM) and Enriched conditioned medium (ECM)] after 9 days of culture. 2B: Mean±SEM live (blue) and CD34⁺ (yellow) cell counts of commercial HSCs in the presence of allogeneic hWJSC-BM and BCM after 9 days of culture. 2C: Mean±SEM live (purple) and CD34⁺ (yellow) cell counts of commercial HSCs in the presence of allogeneic hWJSC-EM and ECM after 9 days of culture. 2D: Contour maps of FACS analysis of commercial CD34+ HSCs when they were cultured in the presence of allogeneic hWJSCs and hWJSC-CM. (a) ECM, (b) hWJSC-EM (c) EM (d) BCM, (e) hWJSC-BM, (f) BM. Each contour map represents the percentage of FITC⁺ cells against unstained controls for CD34+ markers. White peak: Isotype control; Green peak: Experimental sample.

FIGS. 3A-3D: 3A: Mean±SEM colony numbers (CFU assay) of commercial CD34+ HSCs when cultured in the presence of hWJSC-BM and BCM. 3B: Mean±SEM colony numbers (CFU assay) of commercial CD34+ HSCs when cultured in the presence of allogeneic hWJSC-EM and ECM. C: Commercial CD34+ HSC colonies growing in duplicate wells of 24-well plates. (3A, 3B): BCM; (3C, 3D) hWJSC-BM; BM (control). Note greater number of colonies in BCM. 3D: Six different types of colony morphology observed with commercial HSCs cultured in the presence of allogeneic BCM: (1) erythroid colony forming unit (CFUE), (2) granulocyte colony forming unit (CFU-G), (3) granulocyte/macrophage colony forming unit (CFU-GM), (4) erythroid burst forming units (BFU-E), (5) macrophage colony forming unit (CFU-M) and (6) granulocyte-erythrocyte-macrophage-megakaryocyte colony forming unit (CFU-GEMM).

Figure 4A:
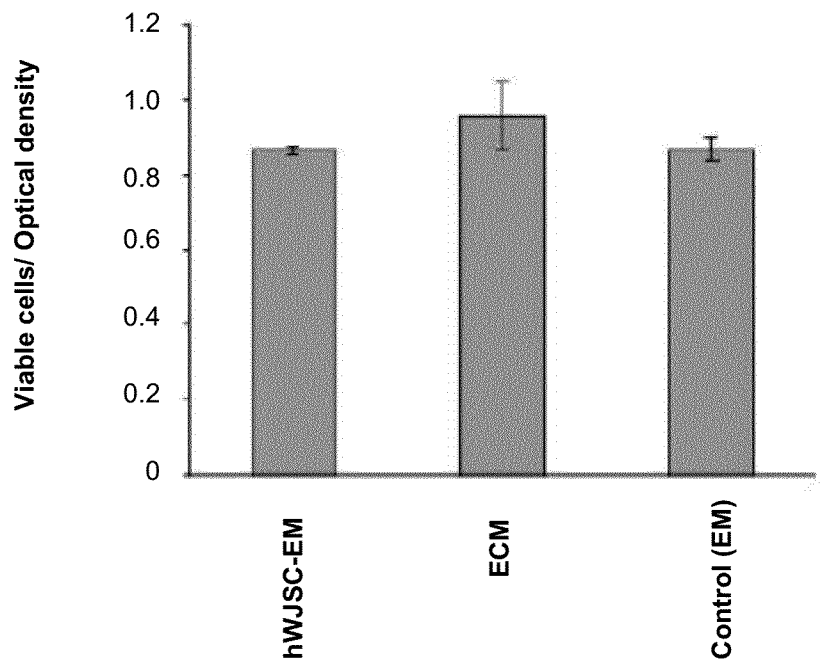
Figure 4B:
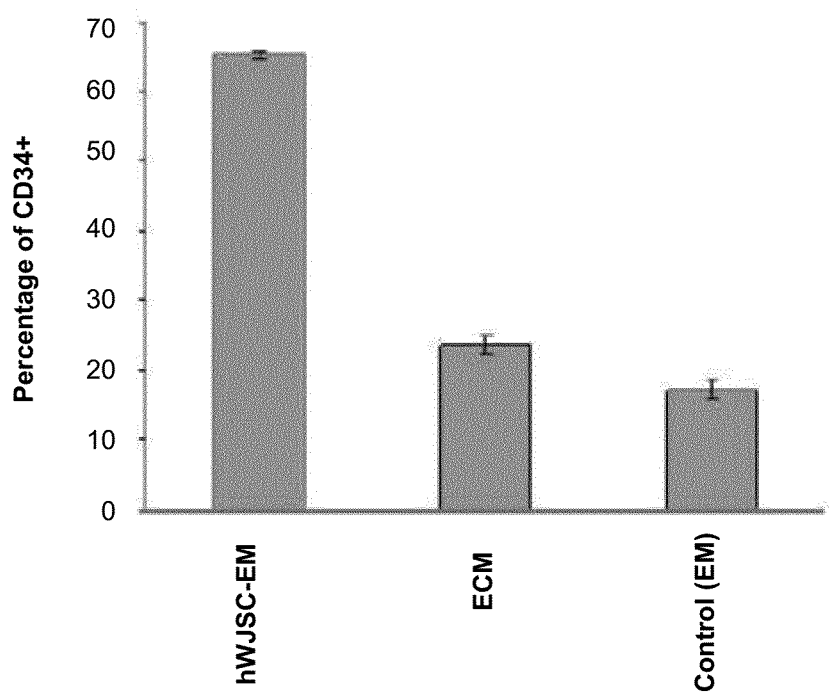

FIGS. 4A-4B: 4A: Mean±SEM proliferation rates of HSCs (MTT assay) in the presence of autologous hWJSC-EM and ECM after 9 days of culture. 4B: Mean±SEM CD34+ HSC percentages after FACS analysis when cultured in the presence of autologous hWJSC-EM and ECM after 9 days of culture.

Figure 5:
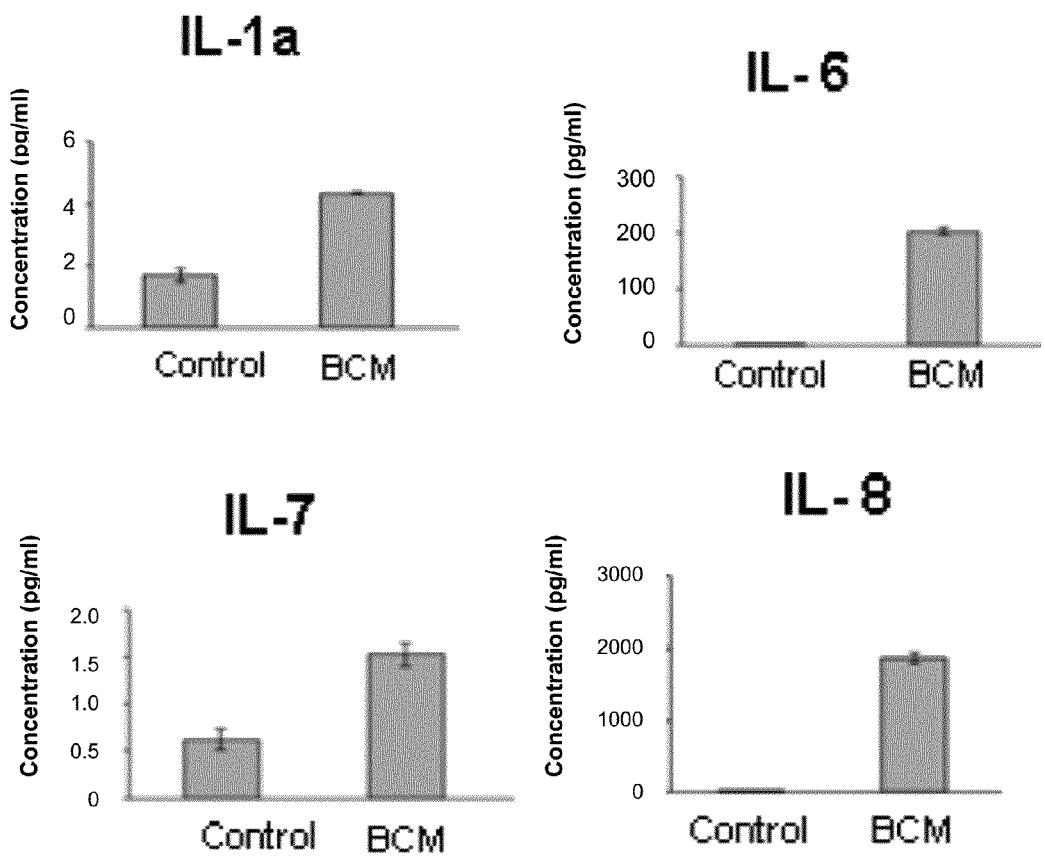
Figure 5:
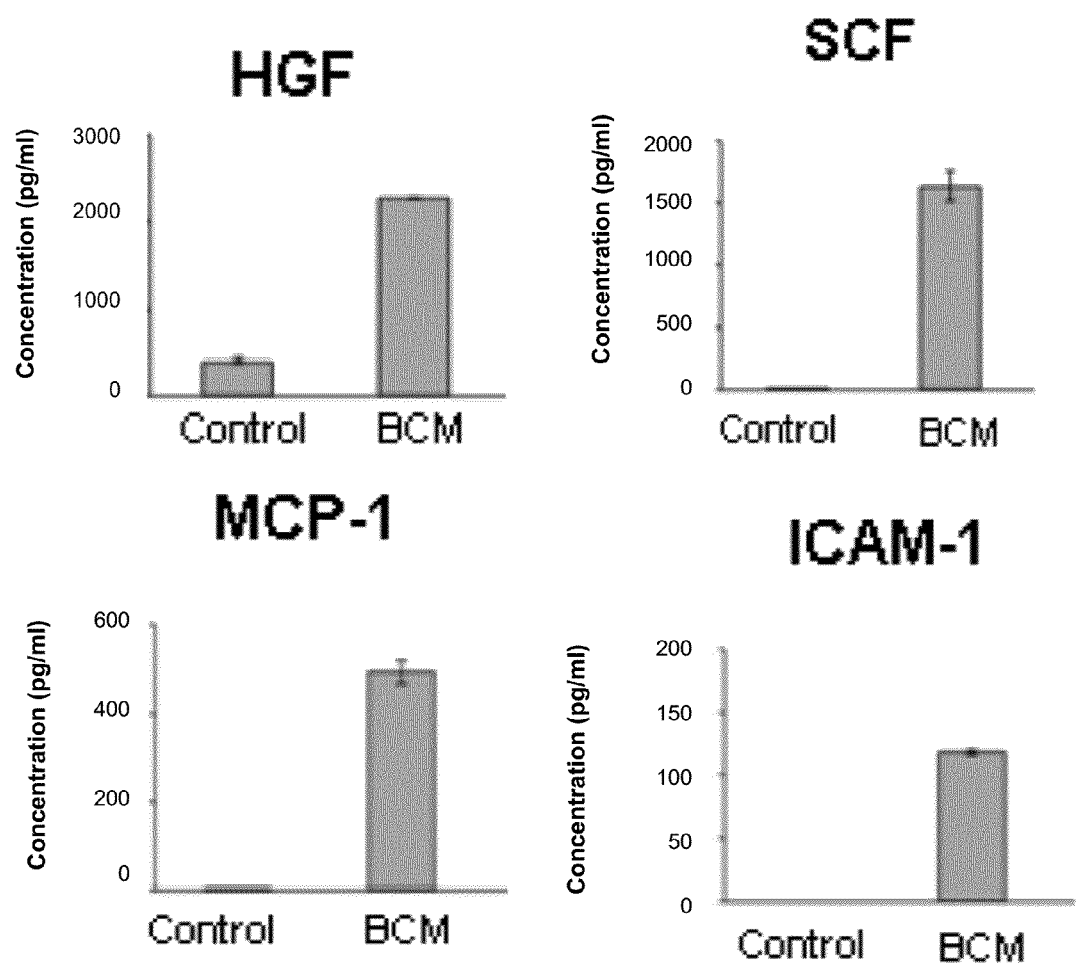

FIG. 5: Proteomic analysis of BCM showing significantly greater Mean±SEM levels (pg/ml) of IL-1a, IL-6, IL-7, IL-8, HGF, SCF, MCP-1 and ICAM-1 compared to controls.

DETAILED DESCRIPTION OF THE INVENTION

Bone marrow mesenchymal stromal cells (BMMSCs) have been used as feeder support for the ex vivo expansion of hematopoietic stem cells (HSCs) but have the limitations of painful harvest, morbidity and risk of infection to the patient. Described herein are methods of using umbilical cord Wharton's jelly MSCs (WJSCs) and/or its conditioned medium (WJSC-CM) for ex vivo expansion of HSCs in allogeneic and autologous settings, which offers advantages over current methods because WJSCs can be harvested in abundance painlessly, are proliferative, hypoimmunogenic and secrete a variety of unique proteins. The invention is exemplified using human HSCs (hHSCs), human WJSCs (hWJSCs) and hWJSC conditioned medium (hWJSCCM or WJSCCM). Specifically, as shown herein, in the presence of hWJSCs and hWJSC-CM, HSCs put out pseudopodia-like outgrowths and became highly motile. Time lapse imaging showed that the outgrowths helped them to migrate towards and attach to the upper surfaces of hWJSCs and undergo proliferation. After 9 days of culture in the presence of hWJSCs and hWJSC-CM, MTT and trypan blue assays showed significant increases in HSC numbers, and FACS analysis generated significantly greater numbers of CD34⁺ cells compared to controls. hWJSC-CM produced the highest number of colonies (CFU assay) and all six classifications of colony morphology typical of hematopoiesis were observed. Proteomic analysis of hWJSC-CM showed significantly greater levels of interleukins (IL-1a, IL-6, IL-7 IL-8), stem cell factor (SCF), hepatocyte growth factor (HGF) and inter-cellular adhesion molecule (ICAM-1) compared to controls indicating that they are likely involved in the HSC multiplication. The methods described herein allow for cord blood banks to freeze autologous WJSCs and umbilical cord blood (UCB) from the same umbilical cord at the same time for the patient for HSC expansion (e.g., ex vivo) and cell based therapies (Fong et al., *J Cell Biochem,* 113:658-668 (2012), which is incorporated herein by reference).

Accordingly, in one aspect, the invention is directed to methods of expanding (proliferating, growing) hematopoietic stem cells (HSCs) comprising culturing (contacting, combining) the HSCs with Wharton's Jelly mesenchymal stem cells (WJSCs), a cell culture medium that has been conditioned with WJSCs, or a combination thereof, thereby producing a HSC culture. The HSC culture is maintained under conditions in which the HSCs expand in the culture, thereby expanding the HSCs.

As used herein, HSCs (e.g., human HSCs) are self renewing stem cells that, when engrafted into a recipient, can "repopulate" or "reconstitute" the hematopoietic system of a graft recipient (e.g., a human; a non-human mammal; an immunodeficient mammal) and sustain (e.g., long term) hematopoiesis in the recipient. HSCs are multipotent stem cells that give rise to (differentiate into) blood cell types including myeloid (e.g., monocytes and macrophages, neutrophils, basophils, eosinophils, erythrocytes, megakaryocytes/platelets, dendritic cells) and lymphoid lineages (e.g., T-cells, B-cells, NK-cells). HSCs express the cell marker CD34 and are commonly referred to as "CD34+". As understood by those of skill in the art, HSCs can also express other cell markers, such as CD133 and/or CD90 ("CD133+", "CD90+").

HSCs are found in bone marrow such as in femurs, hip, ribs, sternum, and other bones of a donor (e.g., vertebrate animals such as mammals, including humans, primates, pigs, mice, etc.). Other sources of HSCs for clinical and scientific use include umbilical cord blood, placenta, fetal liver, peripheral blood (e.g., mobilized peripheral blood, non-mobilized (or unmobilized) peripheral blood), fetal spleen, embryonic stem cells, and aorta-gonad-mesonephros (AGM), or a combination thereof.

As known in the art, HSCs can be obtained from these sources using a variety of methods known in the art. For example, HSCs can be obtained directly by removal from the bone marrow, e.g., in the hip, femur, etc., using a needle and syringe, or from blood following pre-treatment of the donor with cytokines, such as granulocyte colony-stimulating factor (G-CSF), that induce cells to be released from the bone marrow compartment.

As used herein, "Wharton's jelly" refers to a mucilaginous jelly-like substance that occurs in the umbilical cord. Large numbers of bona fide, fully characterized mesenchymal stem cells (MSCs) with high proliferation rates and low population doubling times have been reported in the human umbilical cord Wharton's Jelly (referred to herein as "WJSCs" or "hWJSCs") by several workers. In some aspects, it has been shown that about $4.6 \times 10^6$ fresh live hWJSCs can be harvested from about 1 cm of umbilical cord and the stemness properties of these hWJSCs lasted longer than bone marrow MSCs in vitro (10 vs 3 passages). hWJSCs were also shown to be hypoimmunogenic, thus allowing their use in both autologous and allogeneic settings without the concerns of graft versus host disease, and thaw survival rates of hWJSCs after cryopreservation were greater than 90%.

As described herein, a variety of methods for obtaining WJSCs from umbilical cord are known in the art (e.g., Weiss et al., *Stem Cells*, 24:781-792 (2006), Fong et al., *Reprod Biomed Online*, 15:708-718 (2007), Fong e al., *Reprod Biomed Online*, 21:391-401 (2010), Wang et al., *Stem Cells*, 22:1330-1337 (2004), Romanov et al., *Stem Cells*, 21:105-110 (2003), Sarugaser et al., *Stem Cells*, 23:220-229 (2005), Karahuseyinoglu et al., *Stem Cells*, 25:319-331 (2007), all of which are incorporated herein by reference). For example, as exemplified herein WJSCs can be obtained from one or more pieces of umbilical cord that have been slit open and inverted onto a Petri dish containing an enzymatic solution and incubated at 37° C. in a 5% $CO_2$ in air atmosphere for 45 minutes to allow loosening and separation of the Wharton's jelly from the umbilical cord. The separated Wharton's jelly can then be syringed through an 18 G needle to further break up, and release the WJSCs from, the Wharton's jelly.

The HSCs and/or WJSCs for use in the methods can be obtained from a single donor or multiple donors. In addition, the HSCs and/or WJSCs used in the methods described herein can be freshly isolated, frozen (e.g., cryopreserved), or a combination thereof.

Typically, the HSCs and/or WJSCs are of mammalian origin. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). Examples of mammals include primates (e.g., human, monkeys, chimpanzees), rodents (e.g., rats, mice, guinea pigs), canines, felines, and ruminants (e.g., cows, pigs, horses).

The HSCs and/or WJSCs for use in the methods provided herein can be isolated, pure, or substantially pure. As used herein, "isolated" (e.g., isolated HSCs; isolated WJSCs) refers to substantially isolated with respect to the complex (e.g., cellular) milieu in which it occurs such as isolated from an organ, body, tissue, blood, or culture medium. In some instances, the isolated material will form part of a composition (for example, a crude extract containing other substances), buffer system, culture system or reagent mix. In other circumstances, the material can be purified to essential homogeneity. For example, an isolated composition of HSCs or WJSCs can comprise at least about 50%, at least about 55%, at least about 60%, at least about 65%, at least about 70%, at least about 75%, at least about 80%, at least about 85%, at least about 90%, at least about 95%, or at least about 99% (on a total cell number basis) of all cells present.

In one aspect of the invention, the HSCs and the WJSCs are obtained from different sources (e.g., individuals, such as from the umbilical cords of different individuals). In other aspects of the invention, the HSCs and WJSCs are obtained from a similar (e.g., different individuals such as from the umbilical cords of different individuals of the same species) or the same source (e.g., the same individual such as from the umbilical cord of a single individual). In a particular aspect, the WJSCCM is conditioned with WJSCs that are obtained from the same source as the HSCs.

Thus, for example, in one aspect, the HSCs, the WJSCs and/or the WJSCCM are obtained from different individuals (e.g., syngeneic, xenogeneic). In particular aspects, the HSCs, the WJSCs and/or the WJSCCM are obtained from different individuals of the same species (e.g., allogeneic). In yet other aspects, the HSCs, the WJSCs and/or the WJSCCM are obtained from the same individual (e.g., autologous).

In particular aspects, the HSCs are cultured with WJSCs, WJSCCM or a combination thereof. In one aspect, the HSCs are cultured with a composition comprising, consisting essentially of, or consisting of WJSCs (e.g., allogeneic and/or autologous). In another aspect, the HSCs are cultured with a composition comprising, consisting essentially of or consisting of WJSC conditioned medium (WJSCCM) (e.g., allogeneic and/or autologous). In yet other aspects, the HSCs are cultured with a composition comprising, consisting essentially of, or consisting of WJSCs and WJSCCM (e.g., allogeneic and/or autologous).

As used herein, a medium or cell culture medium is a preparation made specifically for the growth, storage, or transport of cells. The variety of media that exist allow for the culturing of cells in general (e.g., basal medium) or specific cell types (e.g., differential media, selective media, test media, and defined media). The medium can be in a liquid or solid form. In one aspect, solid medium is a liquid medium that has been solidified with an agent such as AGAR or GELATIN. As will be appreciated by those of skill in the art, cell culture media can be prepared using routine skills or obtained from a variety of commercial sources (Fong e al., *Reprod Biomed Online*, 21:391-401 (2010)).

As used herein, a "basal medium" is typically an unsupplemented medium which promotes the growth of many types of cells which do not require any special nutrient supplements for growth (e.g., Eagle's minimal essential medium (EMEM); Dulbecco's modified Eagle's medium (DMEM)). As will be appreciated by those of skill in the art, a basal medium can comprises a variety of components such as one or more amino acids (e.g., non-essential amino acids, essential amino acids), salts (e.g., calcium chloride, potassium chloride, magnesium sulfate, sodium chloride, and monosodium phosphate), sugars (e.g., glucose), and vitamins (e.g., folic acid, nicotinamide, riboflavin, B12), iron and pH indicators (e.g., phenol red). The basal medium can further comprise proteins (e.g., albumin), hormones (e.g., insulin), glycoproteins (e.g., transferrin), minerals (e.g., selenium), serum (e.g., fetal bovine serum), antibiotics, antimycotics and glycosaminoglycans.

As used herein, an "enriched medium" is a cell culture medium to which has been added one or more additives or supplements to enhance the growth of one or more particular cell types. Examples of additive that enhance cell growth include cytokines (e.g., interleukins such as IL-1a, IL-6, IL-7, IL-8), stem cell factors (e.g., SCF), cell adhesion molecules (e.g., inter-cellular adhesion molecule 1 (ICAM-1)), growth factors (e.g., hepatic growth factor), hyaluronic acid, hormones (e.g., insulin), glycoproteins (e.g., transferrin), minerals (e.g., selenium), serum (e.g., fetal bovine serum) and glycosaminoglycans.

As used herein "conditioned medium" is a cell culture media containing biologically active components obtained from cells or tissues that are or were cultured in the medium and have released into the media substances affecting certain cell functions (e.g., growth, lysis). The conditioned medium can, but typically does not, contain the cells that were previously cultured in the medium.

As used herein "basal conditioned medium" is an unsupplemented cell culture medium that has already been used (e.g., partially) to culture cells. Although depleted of some components, it is enriched with cell derived material (e.g., secreted), probably including small amounts of growth factors. In some cases, such cell conditioned medium can, for example, support the growth of cells at much lower density and, can be mixed with some fresh medium.

As used herein an "enriched conditioned medium" is a cell culture medium that has been used (e.g., partially) to culture cells and further comprises additives that enhance cell growth. Examples of additive that enhance cell growth include cytokines (e.g., interleukins such as IL-1a, IL-6, IL-7, IL-8), stem cell factors (e.g., SCF), cell adhesion molecules (e.g., inter-cellular adhesion molecule 1 (ICAM-1)), growth factors (e.g., hepatic growth factor; fibroblast growth factor), hyaluronic acid, and glycosaminoglycans.

In particular aspects, the conditioned medium is a cell culture medium (e.g., basal; enriched) that has been conditioned with WJSCs, referred to herein as Wharton's jelly stem cell conditioned medium (WJSCCM). In a particular aspect, the WJSCCM is human WJSCCM (hWJSCCM) in which the cell culture medium has been conditioned with human WJSCs.

Thus, WJSCCM is conditioned medium that has been previously used to culture WJSCs and typically, but not necessarily, does not include the WJSCs. As will be appreciated by those of skill in the art, various concentrations of conditioned medium can be used in the methods. For example, in the methods described herein, about 40%, 50%, 60%, 70%, 80%, 90% or 100% volume/volume (v/v) conditioned medium diluted in, for example, BM and/or EM, can be used. In one aspect, the medium previously used to culture the WJSCs is a basal medium. In another aspect, the medium previously used to culture WJSCs is a conditioned medium. In yet another aspect, the medium previously used to culture WJSCs is an enriched medium.

As will be appreciated by those of skill in the art, the HSCs can be maintained under a variety of conditions for expansion in culture. For example, the conditions in which the HSCs expand in culture can comprise maintaining the HSC culture at 37° C. in 5% CO2. Further, the HSCs can be cultured for a number of hours or days. In some aspect, the HSCs are cultured for about 1 hour, 5 hours, 10 hours, 15 hours, 20 hours, 1 day, 2 days, 3 days, 4 days, 5 days, 6 days, 7 days, 8 days, 9 days, 10 days 11 days, 12 days, 14 days, etc. As will be appreciated by those of skill in the art, additional media can be added to the culture periodically (e.g., topping up the culture every hour, 2 hours, 4 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 48 hours, etc.).

In the methods of the invention, the degree of expansion of HSCs can be compared to a suitable control. As will be appreciated by those of skill in the art, a variety of controls can be used. For example, the degree of expansion of HSCs obtained using the methods described herein can be compared to the degree of expansion of HSCs that are cultured in the absence of WJSCs, and/or cultured in the absence of a cell culture medium that has been conditioned with WJSCs. In particular aspects, the HSCs are expanded about 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 21-fold, 22-fold, 23-fold, 24-fold or 25-fold compared to a suitable control.

The method can further comprise separating the expanded HSCs from the WJSCs and/or WJSCCM, thereby obtaining isolated HSCs. The method can further comprise storing (preserving) the isolated HSCs (e.g., cryoperserving)

The method can also further comprise culturing the WJSCs in cell culture medium prior to culturing the HSCs. In one aspect, the cell culture medium that has been conditioned with WJSCs is obtained by culturing WJSCs in medium for about 4 hours, 8 hours, 16 hours, 20 hours, 24 hours, 28 hours, 32 hours, 36 hours, 40 hours, 44 hours, or 48 hours, etc.

As described herein allogeneic and autologous WJSCs and WJSCCM (e.g., WJSCs and hWJSC-CM) can be used for ex vivo expansion of UCB HSCs. This discovery provides for a variety of uses.

In one aspect, the invention is directed to a method further comprising introducing (e.g., transplanting) an effective amount of the expanded hematopoietic stem cells into an individual in need thereof. Thus, in another aspect, the invention is directed to a method of transplanting HSCs in an individual in need thereof comprising expanding (proliferating, growing) hematopoietic stem cells (HSCs) ex vivo comprising culturing (contacting, combining) the HSCs with Wharton's Jelly mesenchymal stem cells (WJSCs), a cell culture medium that has been conditioned with WJSCs, or a combination thereof, thereby producing a HSC culture. The HSC culture is maintained under conditions in which the HSCs expand in the culture, thereby expanding the HSCs and producing expanded HSCs. The expanded HSCs are introduced into the individual in need thereof, thereby transplanting HSCs in the individual. The expanded HSCs can be the individual's own HSCs that were expanded ex vivo using the methods provided herein. In a particular aspect, the individual has a malignant hematopoietic disease such as a leukemia or a lymphoma. In other aspects, the individual has a non-malignant hematopoietic disease such as a thalassemia or other blood disorder.

As used herein an "individual" refers to an animal, and in a particular aspect, a mammal. As discussed herein, the terms "mammal" and "mammalian" refer to any vertebrate animal, including monotremes, marsupials and placental, that suckle their young and either give birth to living young (eutharian or placental mammals) or are egg-laying (metatharian or non-placental mammals). Examples of mammals include primates (e.g., human, monkeys, chimpanzees), rodents (e.g., rats, mice, guinea pigs), canines, felines, and ruminants (e.g., cows, pigs, horses).

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined upon consideration the use of well known risk factors. The effective amount of a (one or more) particular compound is determined, in the final analysis, by the physician in charge of the case, but depends on factors such as the exact blood vessel and/or condition (e.g., disease) to be treated, the severity of the condition from which a patient suffers, the chosen route of administration, other drugs and treatments which the patient may concomitantly require, and other factors in the physician's judgment.

An effective amount of expanded HSCs is delivered to an individual in need thereof. As used herein, "effective amount" or "therapeutically effective amount" means an amount of the active compound that will elicit the desired biological or medical response in a tissue, system, subject, or human, which includes alleviation of the symptoms, in whole or in part, of the condition (e.g., disease) being treated.

Any suitable route of administration can be used, for example, transdermal, parenteral (e.g., intravenous, intraarterial, intramuscular, intrasternum), and the like may be employed. Administration can be local or systemic as indicated. The preferred mode of administration can vary depending on the particular agent chosen.

The expanded HSCs can be administered in a single dose (e.g., in a day) or in multiple doses. In addition, the expanded HSCs can be administered in one or more days, months or years (e.g. over several consecutive or non-consecutive days, months, years).

In another aspect, the invention is directed to compositions comprising HSCs and Wharton's Jelly mesenchymal stem cells (WJSCs). The composition can further comprise a cell culture medium that has been conditioned with WJSCs.

In a particular aspect, the composition comprises hematopoietic stem cells (HSCs) and a cell culture medium that has been conditioned with Wharton's Jelly mesenchymal stem cells (WJSCs).

In yet another aspect, the composition comprises "off-the-shelf" allogeneic WJSCs.

The compositions described herein can be administered to an individual as part of a pharmaceutical composition. Formulations will vary according to the route of administration selected (e.g., solution, emulsion or capsule). A "pharmaceutical composition" comprises a (one or more) composition or compound described herein as the active ingredient and inert ingredient(s), such as pharmaceutically acceptable excipients, that make up the carrier. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

EXEMPLIFICATION

Materials and Methods

Derivation, Propagation and Characterization of hWJSCs

Several groups have derived MSCs from various compartments of the human umbilical cord such as the amniotic membrane, subamnion, perivascular areas surrounding the umbilical blood vessels and Wharton's jelly and have referred to such MSCs vaguely as umbilical cord matrix stem cells (UCMSCs). Whether the nature and properties of the MSCs from all these sources are the same is not known. Furthermore, the methods used for derivation of MSCs from the human umbilical cord have also been drastically different between groups with some groups removing the umbilical blood vessels and then scraping off the Wharton's jelly from the inner lining of the umbilical cord, while others keep the umbilical blood vessels intact before scraping off the Wharton's jelly. Some groups tie the ends of the removed umbilical blood vessels into loops and immerse them into an enzymatic solution to collect MSCs from the perivascular areas while some others remove the blood vessels and then dice up the umbilical cord pieces into smaller pieces and immerse them into enzymatic solutions to retrieve MSCs. Based on the method used there is therefore the possibility of heterogeneous populations of cells being harvested. To therefore obtain a more defined homogeneous population of MSCs directly from the Wharton's jelly with minimum or no contamination from other compartments the method of derivation described in Fong et al., *Reprod Biomed Online*, 15:708-718 (2007); Fong e al., *Reprod Biomed Online*, 21:391-401 (2010)).

Approximately 15 to 30 cm long pieces of human umbilical cords were collected after informed patient consent and approval from the Singapore Ministry of Health Institutional Domain Specific Review Board (DSRB). Briefly, the human umbilical cord pieces were cut into smaller 3 cm pieces and washed in Hank's balanced salt solution (HBSS, Invitrogen Life Technologies, Carslbad, Calif.). Each small piece was slit open with sterile forceps and curved scissors and their inner surfaces containing the attached Wharton's jelly were inverted face down into a Petri dish containing a small volume (1.5 ml) of an enzymatic solution that allowed only the Wharton's jelly to come into contact with the enzymes. The enzymatic solution comprised of collagenase type I, collagenase type IV and 100 IU of hyaluronidase (Sigma Chemical Co, USA) in DMEM medium (Invitrogen). The Petri dishes were then incubated at 37° C. in a 5% $CO_2$ in air atmosphere for 45 min to allow loosening and separation of the Wharton's jelly. Any remaining Wharton's jelly that was still attached to the inner surfaces of the cord pieces was carefully separated into fresh medium using the blunt surface of a pair of curved forceps and mixed with the Wharton's jelly in the previous Petri dishes. The final solution containing the gelatinous Wharton's jelly was transferred to a new Petri dish containing 3 ml of fresh DMEM medium and the Wharton's jelly syringed through an 18 G needle to further break up the gelatinous masses to release the hWJSCs. The solution was then collected into sterile 15 ml tubes, centrifuged at 300×g for 10 min, supernatant discarded, and cell pellets resuspended in a hWJSC medium containing 80% DMEM high glucose supplemented with 20% knockout (KO) serum replacement (Invitrogen), 16 ng/ml basic fibroblast growth factor (Millipore Bioscience Research Agents, Temecula, Calif.), 1% non-essential amino acids, 2 mM L-glutamine, 0.1 mM β-mercaptoethanol, 1% insulin-transferrin-selenium (ITS), antibiotic-antimycotic mixture (Invitrogen). The cells were then seeded into sterile T25 plastic tissue culture flasks [Becton Dickinson (BD), USA] and incubated at 37° C. in a 5% $CO_2$ in air atmosphere. When the cells reached confluence in primary culture in approximately 6-7 days, they were passaged by detachment and disassociation with trypsin-EDTA (Invitrogen), centrifugation at 300×g for 10 min, seeding of cell pellets into new T25 flasks and incubation. The phenotype and growth of primary and passaged cells were monitored daily and photographed under inverted phase contrast optics.

The hWJSCs were characterized using the full battery of conventional characterization tests prescribed for MSCs (Dominici, et al., *Cytotherapy*, 8:315-317 (2006); Fong e al., *Reprod Biomed Online*, 21:391-401 (2010)). For all experiments in this study early passaged hWJSCs (P3) were used.

Propagation of HSCs

Approval for purchase and use of commercial cord blood CD34+ HSCs was given by the National University of Singapore Institutional Review Board (NUS-IRB). The frozen CD34+ HSCs were thawed using the instructions and consumables supplied by the manufacturer (Stem Cell Technologies Inc, Singapore). Briefly, the frozen cells were first thawed in a water bath (37° C.) and quickly transferred to a conical tube containing DNase 1 to prevent cell clumping. Approximately, 15 ml of the provided medium [Iscove's MDM (IMDM) containing 10% fetal bovine serum (FBS)] was added into the tube, the solution gently resuspended and then centrifuged at 200×g for 15 min at room temperature. The supernatant was decanted, and cell pellet seeded separately into two types of culture media, Basal medium (BM) and Enriched medium (EM). BM (Stemspan, Serum-free expansion medium, SFEM) comprised of Iscove's MDM medium (IMDM) supplemented with bovine serum albumin (BSA), recombinant human insulin, human transferrin, 2-mercaptoethanol and other supplements. Recombinant hematopoietic growth factors have not been added to this commercial BM. The individual concentrations of these ingredients and the nature of the supplements were not disclosed by the manufacturer (Stem Cell Technologies Inc). The composition of EM was the same as BM but additionally supplemented with CC110 cytokine cocktail which contained a combination of recombinant human cytokines to support the proliferation of human hematopoietic progenitor cells. The nature and concentrations of the individual cytokines were not disclosed by the manufacturer (Stem Cell Technologies Inc). The FACS profile given from the company showed that more than 90% of the cells were $CD34^+$.

The autologous $CD34^+$ HSCs were isolated from up to 100 ml of UCB which was aspirated from the umbilical blood vessels of the same umbilical cords providing hWJSCs using 50 ml syringes and large bore needles. Approval for use of these autologous HSCs was given by the Singapore Ministry of Health Institutional Domain Specific Review Board (MOH-DSRB). The UCB HSCs were isolated using Ficoll-Paque (Stem Cell Technologies) density gradient centrifugation according to a method described by Jaatinen and Laine (2007). Briefly, the UCB was diluted in PBS/EDTA diluents in the ratio of 1:4 and carefully over-layered on the Ficoll-Paque solution and then centrifuged for 40 min. The buffy coat interface layer was collected and washed. CD34+ cells were then enriched from the buffy coat by immuno-magnetic positive selection using the MidiMACS™ system (Miltenyi Biotec, Auburn, Calif.) according to the manufacturer's instructions. Briefly, the mononuclear cells were labeled with CD34 microbeads and added into a MACS LD column attached to a MidiMACS™ magnetic separator. The LD column was then removed from the MidiMACS™ separator and the bound $CD34^+$ cells were eluted with a plunger.

Coculture of Commercial HSCs with Allogeneic hWJSCs

Donor allogeneic hWJSC monolayers (80% confluent) were first inactivated by exposure to 20 µg/mL mitomycin-C (MMC, NUH Pharmacy, Singapore) and incubated at 37° C. for 2.5 h. After incubation, the hWJSCs were washed thoroughly twice with phosphate buffered saline (PBS) followed by one wash with hWJSC medium. The cells were then disassociated with trypsin-EDTA (Invitrogen) and 25,000 inactivated hWJSCs were seeded per well in two sets (A and B) of 24-well plates (Nalge Nunc International, Rochester, N.Y., USA). After 24 h when the hWJSCs had attached to the plastic surfaces of the wells in both sets of plates (60%-70% confluence), the hWJSC medium was completely removed and an equal number of commercial CD34+ HSCs (25,000 in 0.5 ml of BM) were seeded in each well of Plates A and similar numbers of HSCs in 0.5 ml of EM seeded in each well of Plates B. Plates A (hWJSC-BM) and B (hWJSC-EM) were incubated for 9 days at 37° C. in a 5% $CO_2$ in air atmosphere with topping up with 0.25 ml of BM or EM every 48 h, after which the HSCs were subjected to a battery of assays to evaluate cell behavior and proliferation.

Culture of Commercial HSCs with Allogeneic hWJSC Conditioned Medium (hWJSC-CM)

Early passaged hWJSCs (3P) were first grown to 70% confluence in hWJSC medium followed by removal of the spent medium. The monolayers were then washed with PBS twice to remove any residual hWJSC medium and the cells grown in BM for 24 h after which the conditioned BM was separated. This medium was referred to as Basal Conditioned Medium (BCM). The same procedure was carried out with EM and this conditioned medium was referred to as Enriched Conditioned Medium (ECM). Both BCM and ECM were filtered by passing through a 0.22 µm filter. Freshly thawed commercial $CD34^+$ HSCs (25,000) were seeded in each well of 24-well plates (Nalge) and grown separately in 0.5 ml of BCM or ECM for 9 days at 37° C. in 5% $CO_2$ in air with topping up with 0.25 ml of BCM or ECM every 48 h.

After 9 days of culture, the CD34+ HSCs were subjected to the same battery of assays as the coculture plates above to evaluate cell behavior and proliferation. Commercial $CD34^+$ HSCs and MMC-treated hWJSCs were cultured alone and in parallel with the experimental plates for 9 days in the four different culture media (BM, BCM, EM, ECM) to act as controls.

Culture of Autologous HSCs with hWJSCs and hWJSC-CM from the Same Umbilical Cords Twenty five thousand MMC-treated or -untreated hWJSCs were seeded in each well of 24-well culture plates (Nalge) containing EM or WJSC medium and incubated at 37° C. in a 5% $CO_2$ in air atmosphere. When the hWJSCs had adhered in each well (60%-70% confluence), the EM or WJSC medium was removed and an equal number of autologous HSCs (in 0.5 ml of EM) that were harvested from the same umbilical cord as the hWJSCs, were added to each well and incubated for 9 days with topping up with 0.25 ml of fresh EM every 48 h. Separately, 25,000 autologous HSCs in 0.5 ml of ECM were seeded into each well of 24-well plates (Nalge) and incubated at 37° C. in a 5% $CO_2$ in air atmosphere and incubated for 9 days with topping up with 0.25 ml of fresh ECM every 48 h. After 9 days, the autologous HSCs in both hWJSC and hWJSC-CM plates were subjected to the MTT assay for evaluation of cell proliferation and FACS analysis for calculation of $CD34^+$ cell counts.

Phase Contrast Optics and Scanning Electron Microscopy (SEM)

The interaction of the commercial and autologous HSCs with the hWJSCs and hWJSC-CM were studied using time lapse imaging, phase contrast optics and conventional scanning electron microscopy (SEM). Videos and images of the behavior of the cells were captured using a digital camera at regular intervals when the cells were monitored during the 9 days of culture.

Cell Proliferation: MTT Assay

10 µl MTT reagent (final concentration of 0.5 mg/ml) was added to the culture media in the hWJSC and hWJSC-CM plates (A and B) after the 9 days of exposure to HSCs, and the plates were incubated for 4 h until the appearance of visible purple precipitate. The plates were then centrifuged at 300×g for 5 min to spin down the HSCs, medium decanted and 100 µl of detergent reagent added into each well. The plates were incubated in the dark at 37° C. in a 5% $CO_2$ in air atmosphere for 2 h and absorbance measured at 570 nm against a reference wavelength of 630 nm using a spectrophotometer equipped with micro plate ELISA reader.

Trypan Blue Vital Cell Counts

Aliquots of the cultured CD34+ HSCs from the hWJSC, hWJSC-CM and control plates after 9 days of culture were taken and stained with 0.4% Trypan Blue (vital dye) (Sigma) for 1 min at room temperature. The number of live HSCs (unstained) were counted using a hemocytometer.

Flow Cytometric Analysis

The cultured CD34+ cells from the hWJSC, hWJSC-CM and control plates were blocked with 10% normal goat serum (NGS) (Invitrogen) to prevent non-specific binding and then incubated with primary antibodies (1:100) for the CD34 marker (Biolegend, San Diego, Calif.) for 30 min, followed by a PBS wash and incubation with Alexa Fluor®488 (1:750) secondary antibody for 30 min (Invitrogen). The cells were then re-suspended in 10% NGS, filtered through a 40 µm nylon strainer to remove any cell clumps and analyzed using a CyAn™ ADP Analyzer (Beckman Coulter, Fullerton, Calif.).

Colony Forming Assay

The cultured CD34+ cells from the hWJSC, hWJSC-CM and control plates were separated, centrifuged 300×g for 5 min, supernatant decanted and cell pellets seeded into wells of 24-well plates (Nalge) containing 0.5 ml of semisolid methylcellulose in Methocult H4435 medium. This medium was a commercial medium from Stem Cell Technologies Inc and contained IMDM, BSA, 2-mercaptoethanol, recombinant human stem cell factor (rhSCF), granulocyte colony stimulating factor (rhG-CSF), granulocyte macrophage-CSF (rhGM-CSF), interleukin-3 (rhIL3), interleukin-6 (rhIL6), erythropoietin (rhEPO) and supplements. The individual concentrations of each supplement was not disclosed by the manufacturer. Six different cell densities ranging from 300 to 10,000 cells were seeded per well and plates incubated at 37° C. in a 5% $CO_2$ in air atmosphere. After 14 days, colonies that were formed were counted and analyzed for morphology. Colony morphologies were classified according to that described in the manufacturer's manual (Stem Cell Technologies Instruction Manual) as (1) colony forming unit-erythroid (CFUE), (2) colony forming unit-granulocyte (CFU-G), (3) colony forming unitgranulocyte/macrophage (CFU-GM), (4) burst forming unit-erythroid (BFU-E), (5) colony forming unit-macrophage (CFU-M) and (6) colony forming unit-granulocyte/erythrocyte/macrophage/megakaryocyte (CFU-GEMM). Colony forming unit numbers were calculated by dividing the number of colonies at day 14 by the number of cells plated and multiplying this value by 10,000 which reflected the colony forming ability of 10,000 cells.

Cytokine Analysis of hWJSC-CM Using the Multiplex Luminex® Beads Assay

Differential cytokine analysis of BCM and controls was carried out using the Bio-Rad Express assay kit for human group I and II cytokines (Bio-Rad Laboratories, Singapore Pte Ltd). The 96-well microtitre plates provided with the kit were wetted with 100 µl of wash buffer and 50 µl of beads were added to each well. The BCM samples (50 µl) were diluted in equal volumes of assay diluent and 50 µl of the diluted sample and standards was added to the beads in each well. The plates were incubated for 1 h at room temperature on a shaker in the dark and the assays were run in duplicate. After incubation the plates were washed twice in buffer and 100 µl of secondary biotinylated antibody (1:10 dilution in antibody diluent) provided with the kit was added to each well. The plates were further incubated at room temperature for 1 h in the dark and then washed twice with buffer. Then 100 µl of streptavindin-PE provided with the kit was added to each well and the plates incubated for 30 min at room temperature in the dark. The wells were finally washed thrice, filled with 100 µl of wash buffer and the plates then incubated for 2-3 min at room temperature in the dark. The plates were then read on a Bio-plex array reader and data subsequently analyzed using the Bio-plex manager software, version 3.

Statistics

All results were expressed as Mean±SEM and statistically significant differences between different groups were calculated using the two-tailed student's t-test (SPSS 13). A value of $p<0.05$ was considered as statistically significant.

Results

Culture of Commercial HSCs with Allogeneic hWJSCs/hWJSC-CM

Cell Behavior

Human Wharton's jelly stem cells derived by the method in this study displayed a short fibroblast-like morphology with short population doubling times of approximately 24 h and high proliferation. They met the criteria for MSCs as recommended by the International Society of Cellular Therapy. They were plastic adherent, could be differentiated into several lineages and had high expression levels of CD73, CD13, CD29, CD44, CD90, CD105 and D146, and low level expression for CD45, CD10, CD14, CD34, CD117 and HLA-DR surface molecules. They retained their stemness characteristics for up to 10 passages when characterized with the full battery of characterization tests for MSCs. Mitomycin-C was effective in stopping their multiplication and keeping them as 70%-80% confluent monolayers for the purpose of this study.

Figure 1A:
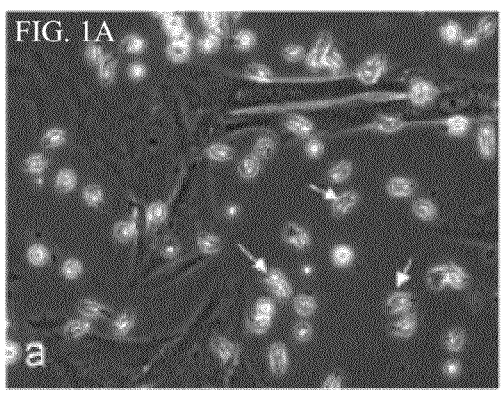
FIGS. 1A-1F: 1A: Phase contrast image showing HSCs putting out pseudopodia-like outgrowths (arrows) in the presence of adherent hWJSCs (×200); 1B: Phase contrast image showing HSCs migrating towards the upper surfaces of hWJSCs, attaching to them and undergoing multiplication (×200); 1C: Phase contrast image showing several HSCs putting out pseudopodia-like outgrowths (arrows) in hWJSC-CM (×200); 1D: Phase contrast image showing very few HSCs having pseudopodia-like outgrowths in controls ([(Basal medium (BM)/Enriched medium (EM)] (×200). 1E: Scanning electron micrograph (low magnification) showing HSCs loosely attached to upper surfaces of hWJSC monolayers; 1F: Scanning electron micrograph (high magnification) showing HSCs undergoing mitosis on surface of hWJSC.
Figure 1B:
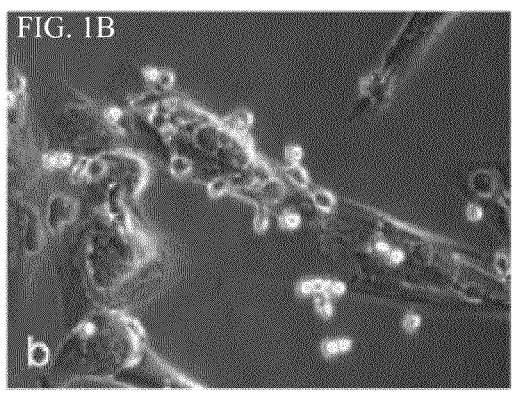
Figure 1C:
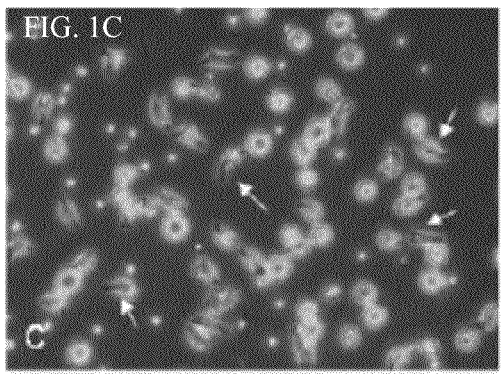
Figure 1D:
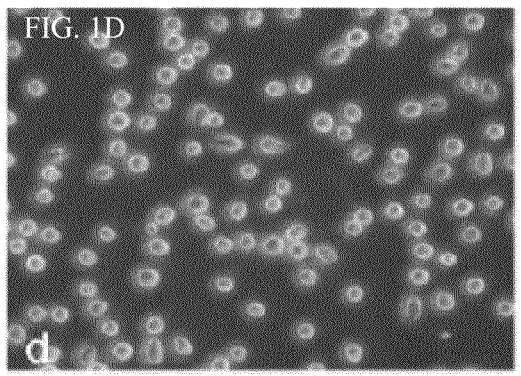
Figure 1E:
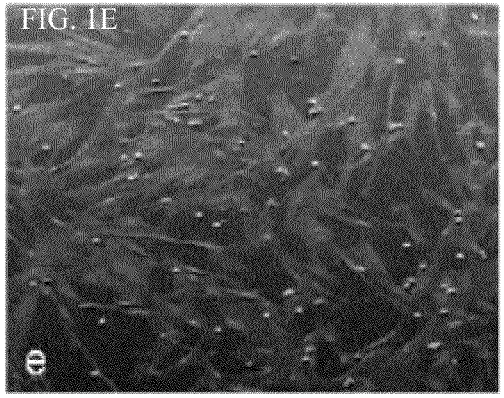
Figure 1F:
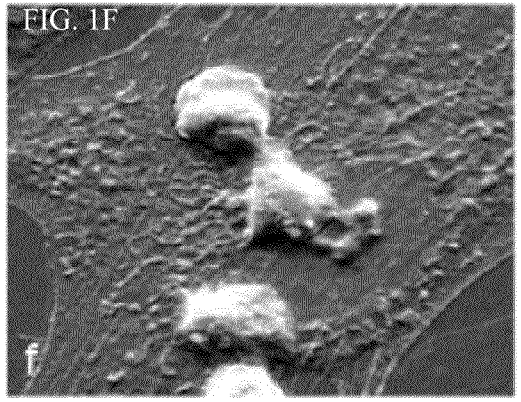

Over 90% of the commercial HSCs that were purchased tested positive for CD34 markers at the time of this study. Time lapse imaging over a 12 h period and phase contrast optics showed that most of the HSCs changed from a circular to elongated morphology, put out pseudopodia-like outgrowths and migrated towards the bodies of the hWJSCs, loosely attaching to them and undergoing mitosis (FIGS. 1A, 1B). When the HSCs were exposed to hWJSC-CM, they also became active and showed similar elongated morphology with pseudopodia-like outgrowths (FIG. 1C). Such HSC behavior lasted throughout the 9 day period and was not seen in controls (FIG. 1D). Scanning electron micrographs confirmed the mitotic activity of the HSCs on the hWJSCs and showed that most of the HSCs attached to the upper surface of the hWJSC monolayer with very few cells migrating beneath (FIGS. 1E, 1F).

MTT Assay

Figure 2A:
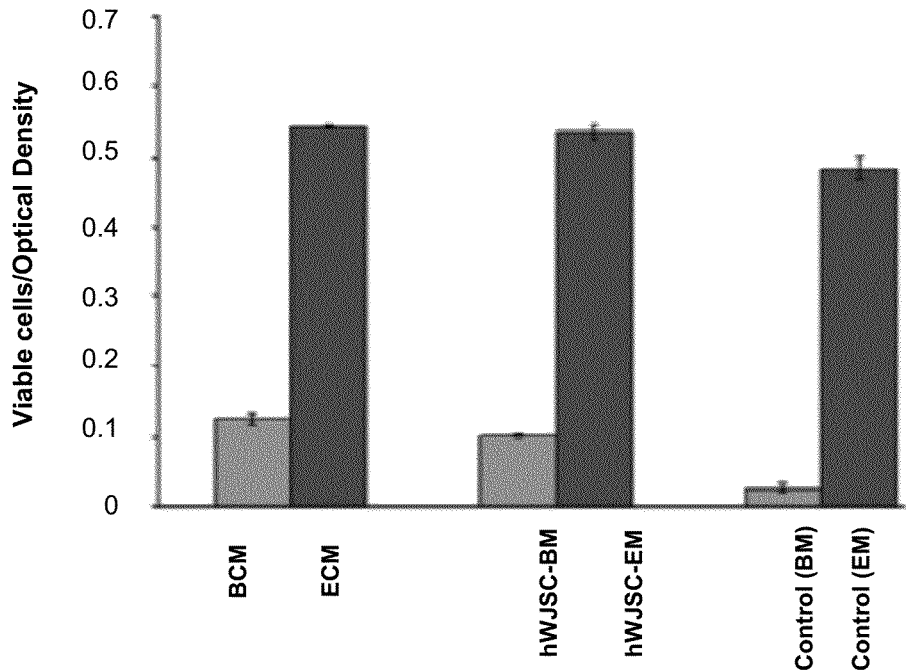
FIGS. 2A-2D: 2A: Mean±SEM proliferation rates of commercial HSCs (MTT assay) in the presence of allogeneic hWJSCs (hWJSC-BM and hWJSC-EM) and hWJSC-CM

The Mean±SEM HSC proliferation rates in the presence of hWJSC-BM and BCM were significantly greater than controls (FIG. 2A). The proliferation rates for hWJSC-EM and ECM were also greater than their controls and was significant (FIG. 2A).

Live Cell Counts (Trypan Blue Staining)

Figure 2B:
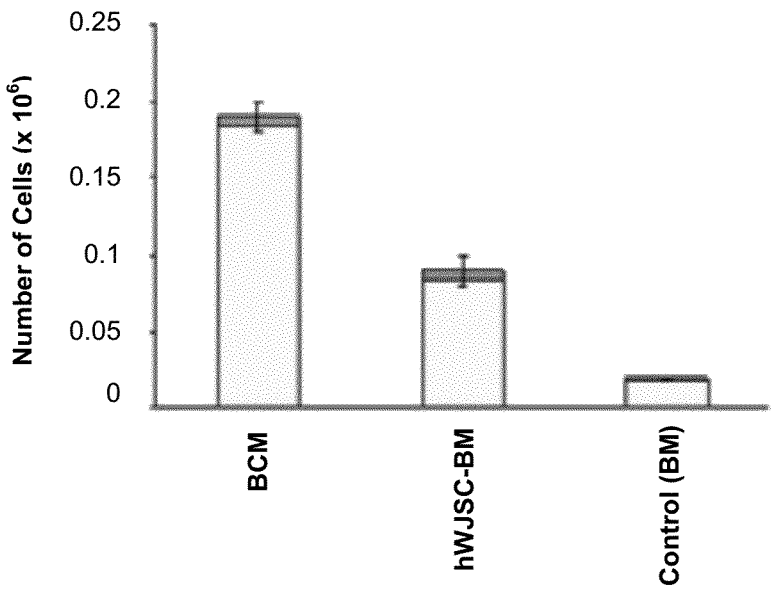
Figure 2C:
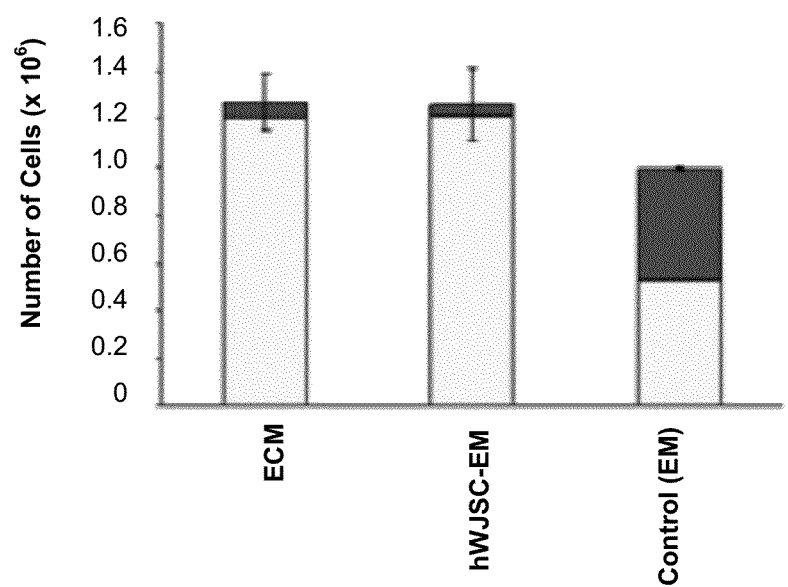

When Trypan blue staining was used to evaluate the vitality of the expanded HSCs, the overall Mean±SEM live HSC counts (including $CD34^+$ cell counts) in the hWJSC-BM and BCM culture environments were significantly greater than controls (FIG. 2B). The overall Mean±SEM live HSC counts for hWJSC-EM and ECM were not significantly greater than their controls but the $CD34^+$ cell counts were significantly different (FIG. 2C).

Flow Cytometric Analysis (FACS)

Figure 2D:
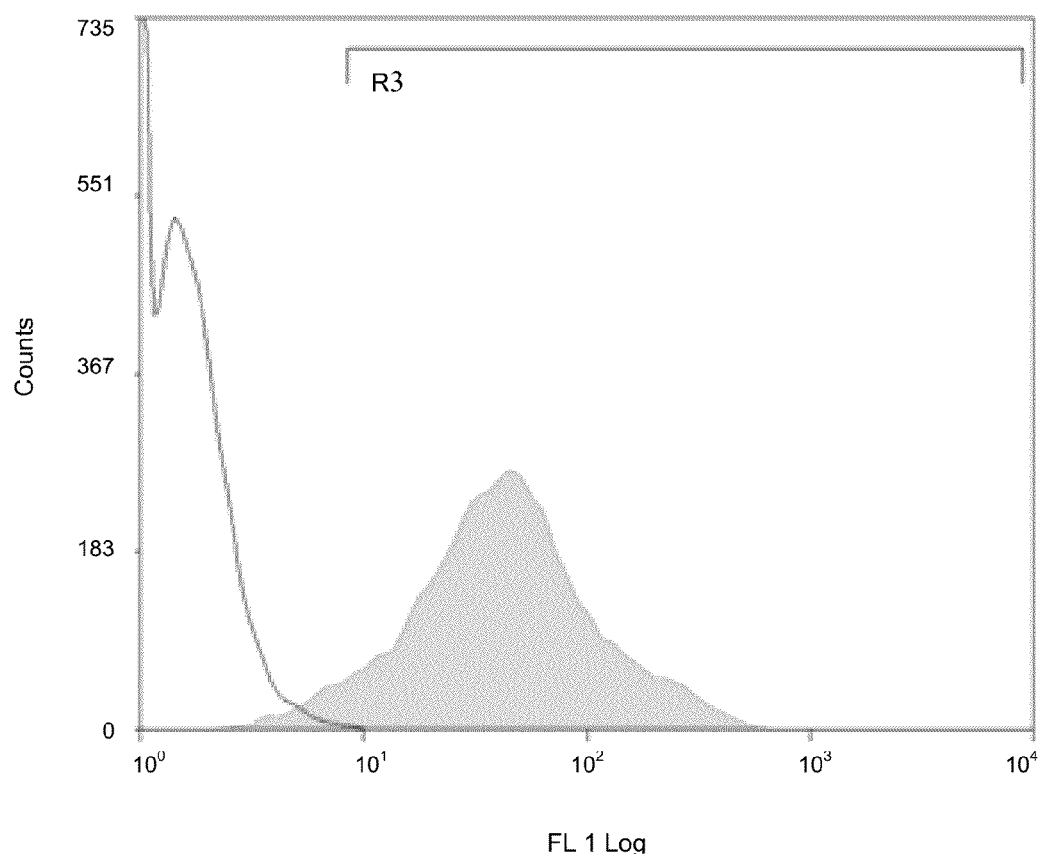
Figure 2D:
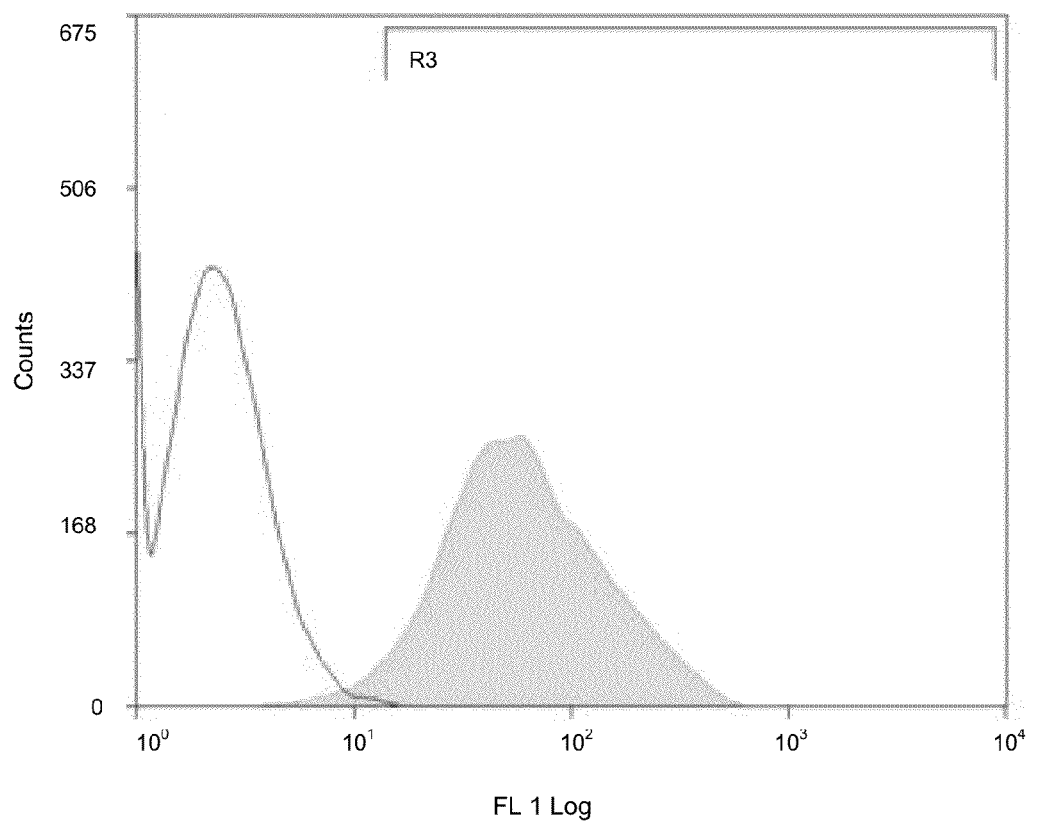
Figure 2D:
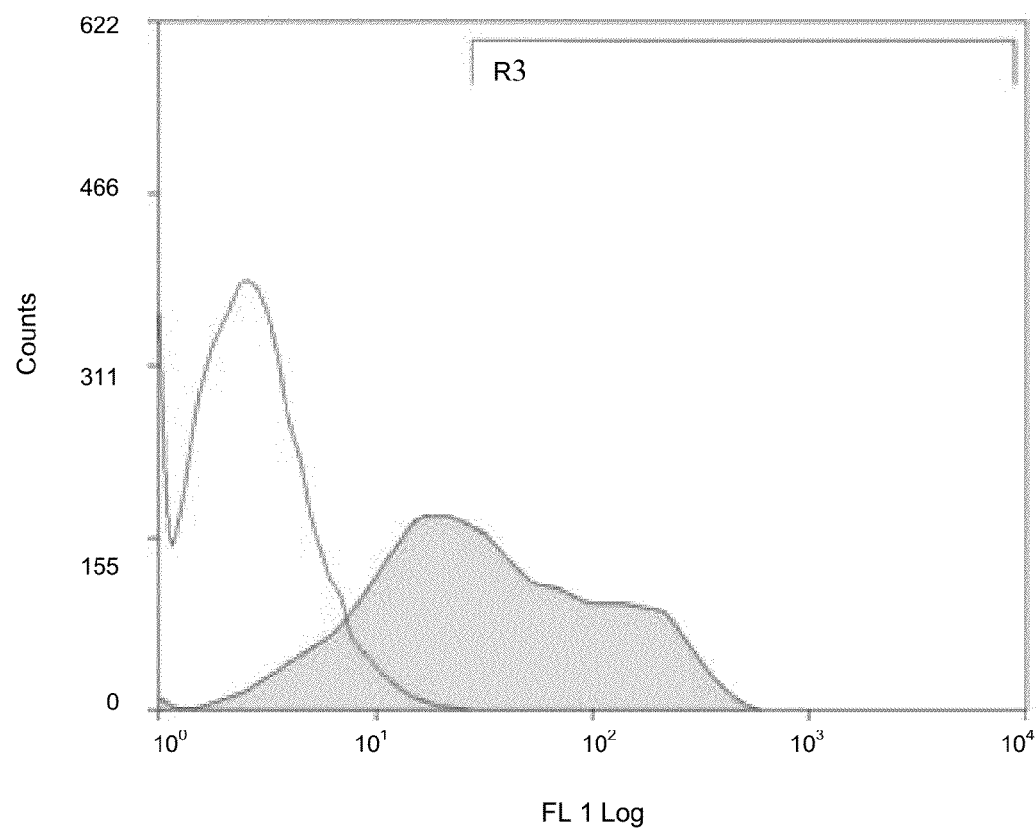
Figure 2D:
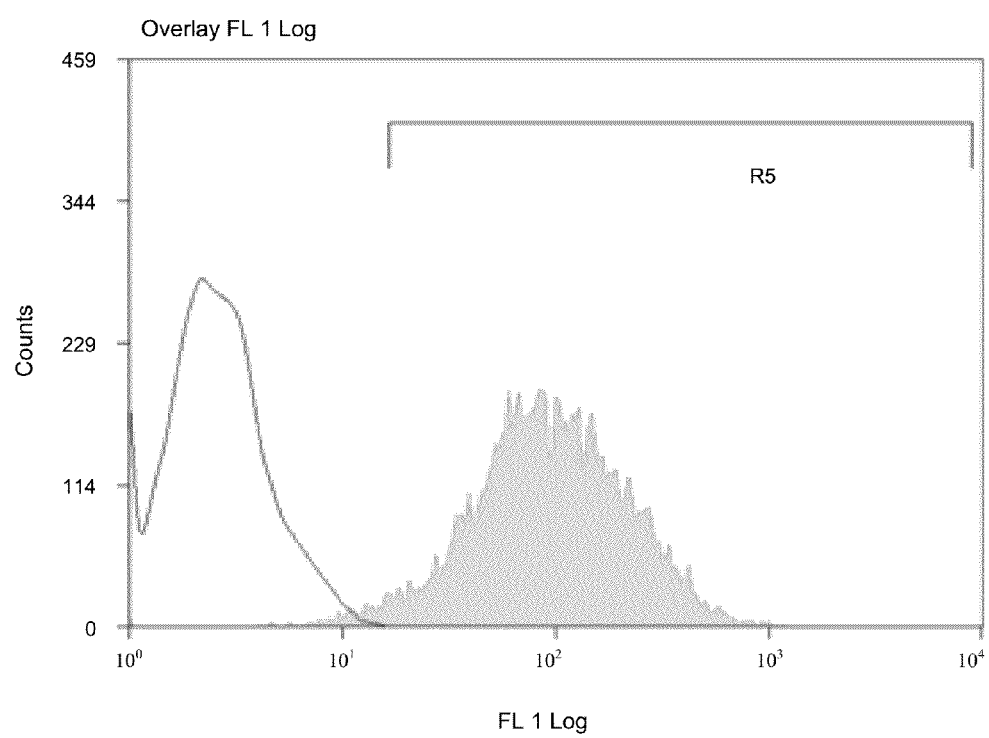
Figure 2D:
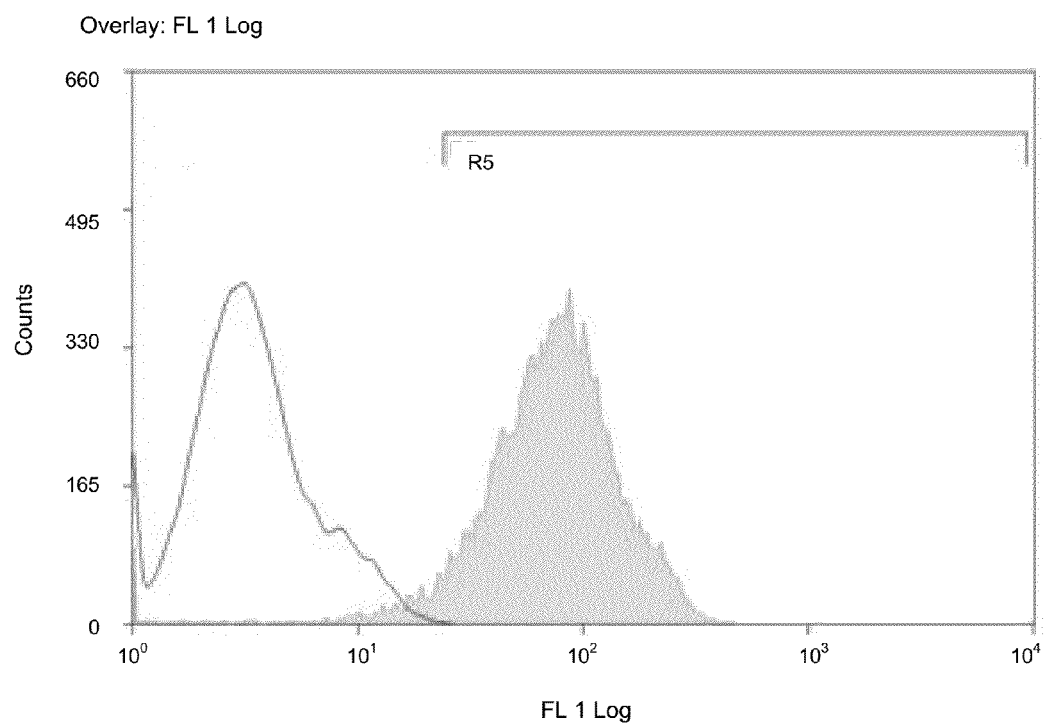
Figure 2D:
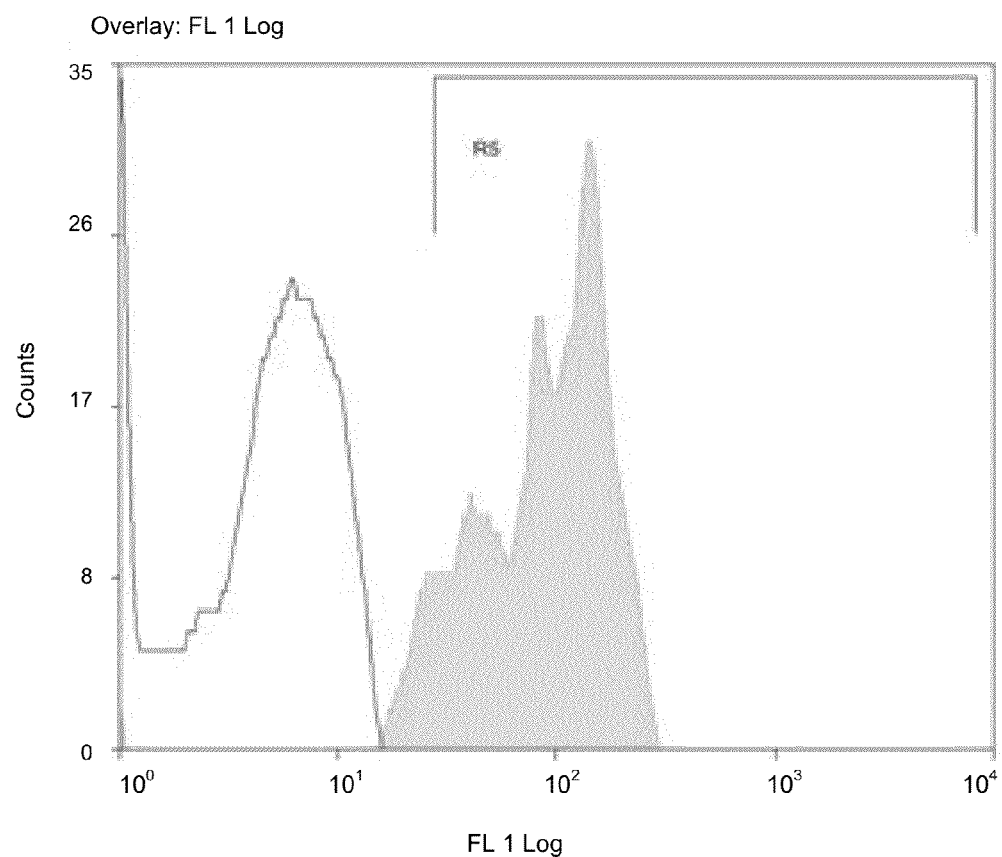

FACS analysis showed that the hWJSCs and hWJSC-CM culture environments yielded greater numbers of $CD34^+$ HSCs compared to controls (hWJSC-BM: 93.91%; BCM: 96.91%; hWJSC-EM: 96.07%; ECM: 94.71%; BM: 86.68%; EM: 52.97%) (FIG. 2D).

Colony Forming Unit (CFU) Assay

Figure 3A:
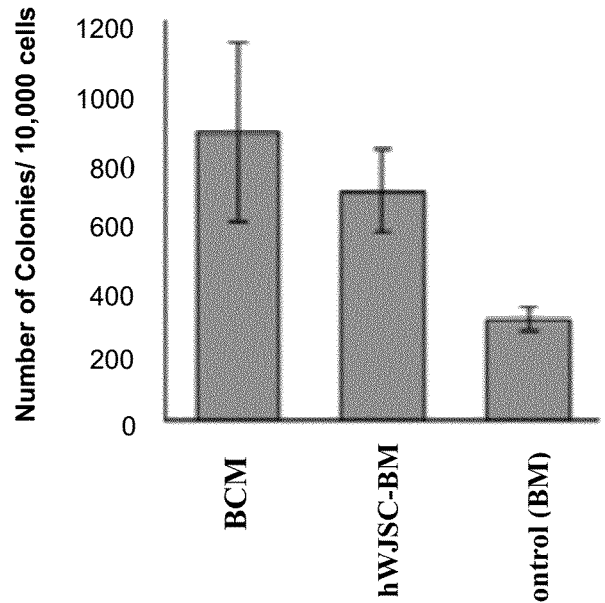
Figure 3B:
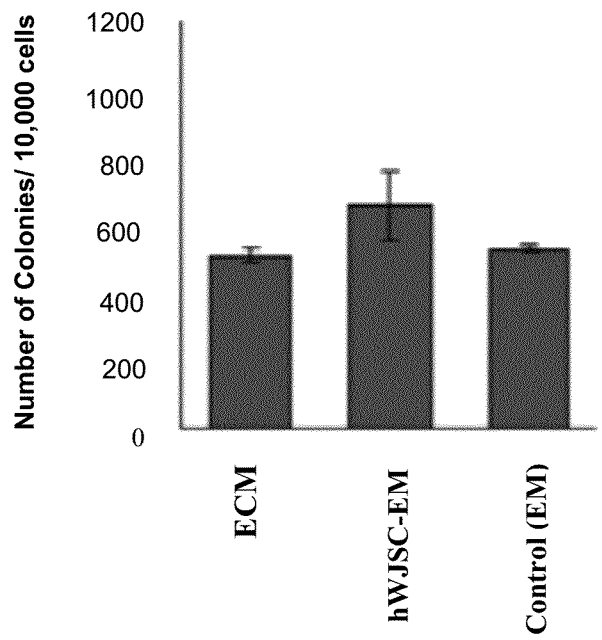
Figure 3C:
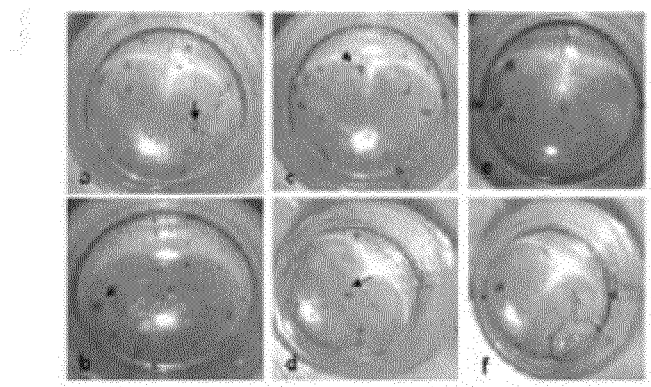
Figure 3D:
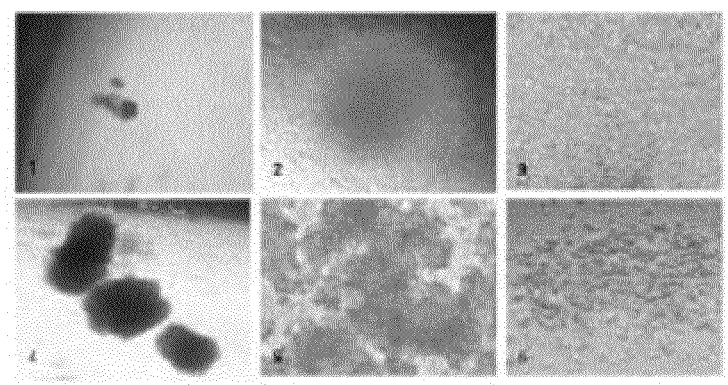

The CFU assay showed that the Mean±SEM number of colonies in the hWJSC-BM (688±125) and BCM (864±272) culture environments were greater than their controls (304±34) (FIGS. 3A, 3C). The hWJSC-EM (656±102) culture environment also generated a greater number of $CD34^+$ colonies than its controls (528±11) but these values were not as high as those with BCM (FIG. 3B). All 6 types of colony morphology for normal hematopoiesis (CFU-E, CFU-G, CFU-GM, BFU-E, CFU-M and CFU-GEMM) were observed in the experimental arms compared to controls (FIG. 3D).

Culture of Autologous HSCs with hWJSCs/hWJSC-CM from the Same Umbilical Cords When fresh unfrozen autologous HSCs from the same patient's umbilical cord were cultured in the presence of its own inactivated hWJSCs or its hWJSC-CM for 9 days using the same protocols as for the commercial HSCs, similar trends in cell behavior, cell proliferation, colony counts and colony morphology for $CD34^+$ cells were observed (FIGS. 4A, 4B).

Proteomic Profiles in hWJSC-CM

Concentration levels of certain members of the interleukin family (IL-1a, IL-6, IL-7, IL-8), hepatocyte growth factor (HGF), stem cell factor (SCF), monocyte chemotactic protein-1 (MCP-1) and inter-cellular adhesion molecule 1 (ICAM-1) were significantly increased in the BCM compared to controls (FIG. 5). Of these factors, the levels for IL-6, IL-8, HGF, SCF and ICAM-1 were extremely high compared to controls (IL-6: 203.82±6.78 vs 0.16±0.01; IL-8: 1875.94±74.33 vs 4.72±0.14; HGF: 2272.81±5.65 vs 409.05±29.06; SCF: 16,390.19±0.15 vs 4.74±0.02; ICAM-1: 118.86±2.09 vs 0 or <than detectable range).

DISCUSSION

Since HSCs can differentiate into the full spectrum of mature blood cells they have been used clinically for the treatment of malignant and non-malignant diseases of the hematopoietic system. Unfortunately however, bone marrow HSCs have the disadvantages of insufficient numbers, painful harvest, potential morbidity and risk of infection. The low HSC numbers present in UCB together with their slow self-renewal in vitro has limited their use to only children and not adults. Two therapeutic strategies have therefore been explored by cord blood banks to help increase HSC numbers for treatment. These include (1) double cord blood transplant (CBT) and (2) ex vivo expansion. Double CBT significantly delayed engraftment and increased engraftment failure and only one of the CBT units predominated during engraftment. It was shown that increasing the dose of the cell subpopulations responsible for rapid engraftment improves neutrophil and platelet counts for engraftment and reduces engraftment failure. Described herein is the development of reliable ex vivo HSC expansion methods.

A variety of stromal cells have been studied as matrices for ex vivo expansion of HSCs and these include in-house derived primary cell monolayers, genetically modified cytokine-releasing cells, bone marrow MSCs (BMMSCs) and immortalized BMMSCs. The mechanism of action of such feeder-cell matrices was the production of a sustained release of secretory molecules that promote HSC self-renewal and maintenance. Fresh patient-aspirated or commercial BMMSCs thus far have been the cell of choice for stromal support of HSCs on the premise that such MSCs are normally resident in the bone marrow and their natural in vivo role was to provide a scaffold for the expansion of neighboring HSCs. However, because of the pain and risk of infection in harvesting fresh BMMSCs and the variability and cost in using commercial BMMSCs the use of UCB-MSCs have been explored for ex vivo HSC expansion. Unfortunately, UCB-MSCs also have their own limitations in that some groups were successful in isolating MSCs from UCB while others failed or obtained very low MSC numbers. In fact only 29 MSC-like colonies were isolated in 17 of 59 processed cord blood units with optimal cell growth being reached as late as 20 days in culture. hWJSCs or hWJSC-CM is available in abundance and is an attractive source of allogeneic or autologous support for ex vivo HSC expansion. Using the protocol described herein, the derivation efficiency for hWJSCs was 100% (hWJSCs were harvested and successfully propagated in all of 12 different patients) and hWJSC numbers of approximately $4-5 \times 10^6$ cells/cm of umbilical cord were consistently obtained. Such MSC numbers without serial culture are very much higher than what is available in bone marrow or UCB.

Time lapse imaging, phase contrast optics and SEM showed that in the presence of hWJSCs or its hWJSC-CM the HSCs began to put our pseudopodia-like outgrowths to help them migrate towards the surface of the stromal hWJSCs looking for niches to attach and proliferate. Such outgrowths have been previously described as 'fleet feet' or 'uropods'. Rapid motility and directed migration towards stromal cells with membrane modulation were also observed using high-speed optical sectioning microscopy and inverted fluorescent video microscopy. In fact, Alakel et al., (2009) showed that direct contact of HSCs with MSCs affected migratory behavior and gene expression profiles of $CD133^+$ HSCs during ex vivo expansion. Additionally, it was postulated that specific stem cell niches within the stromal cell monolayers played a role in HSC migration and proliferation and the MSC surface was the predominant site of HSC proliferation while the compartments beneath the MSC layer mimicked the stem cell niche for more immature cells.

hWJSCs have been shown by many workers to secrete a wide variety of factors including members of the interleukin family, GAGs, hyaluronic acid, cell membrane proteins, cell adhesion molecules, cadherins and growth factors. The results of proteomic analysis in the present study are consistent with these reports with levels of most of these proteins being much higher than that observed in BMMSC and other stromal cell types. The members of the interleukin family specifically IL-6 and IL-8 and the growth factors (SCF, HGF) may be the important players in bringing about the ex vivo HSC expansion as their values in the BCM in this study were extremely high. IL-6 has been reported to stimulate hematopoiesis and IL-8 enhances the proliferation of CD34+ cells while SCF and HGF were shown to be effective in hematopoietic progenitor cell maintenance. Additionally, hWJSCs naturally secrete high levels of hyaluronic acid (HA) and glycosaminoglycans (GAGs) which are the building blocks of the extracellular matrix. Interestingly, it was recently shown that when heparan sulfate (a member of the GAGs family) was administered alone to CD34+ cells it helped to expand and maintain the morphology of blood lineages in vitro.

The hWJSC-CM in the present study provided as good or better support than the cells themselves for HSC expansion. This would be more appealing to regulatory bodies for clinical application as hWJSC-CM is a non-cellular liquid, defined, safer and excludes the potential transmission of adventitious agents from stromal supporting cells to the HSCs. Bhatia et al., (1997) reported the expansion of long term culture-initiating cells (LTC-ICs) and colony forming cells (CFC) when they used a bone marrow stromal-conditioned medium supplemented with IL3 and macrophage inflammatory protein 1 (MIP-1a). hWJSC-CM is not only naturally rich in these specific agents reported by Bhatia et al., (1997) but possess additional useful interleukins (IL-1a, IL-6, IL-7, IL-8) and growth factors and as such would not need any supplementation to bring about even greater desirable effects.

The logistical limitations of using BMMSCs from a family member of the patient as stromal support for ex vivo expansion of HSCs at the time of treatment has been highlighted. These limitations included (1) the appropriate family member not always being available to donate the bone marrow and (2) and the long time taken to not only generate sufficient BMMSCs (3 weeks) but also carry out coculture expansion (2 weeks) to provide adequate expanded HSCs (5 weeks) since the disease progression was very rapid in some leukemic patients. Therefore the availability of a source of 'off-the-shelf' GMP-compliant allogeneic MSCs for immediate use alleviates this logistic problem. The results described herein showed that allogeneic hWJSCs are an attractive source of such 'off-the-shelf' MSCs.

The results herein also demonstrated that autologous hWJSCs harvested from the same patient's umbilical cord provided a useful source of stromal support cells for CD34+ expansion. This is ideal as there are no immunogenic issues when it comes to cell matching even though allogeneic hWJSCs in general are considered hypoimmunogenic. Harvesting of hWJSCs takes only a few hours and from a practical point of view, it is possible to freeze and store UCB-HSCs and hWJSCs of the same patient on the same day in a dual chamber blood collection bag. When the HSCs are needed, the hWJSCs could be thawed, confluent monolayers established to generate 24 hWJSC-CM which can then be used for the expansion of HSCs when their numbers are low. This approach will avoid the need for discarding HSC samples that are low in numbers as is practiced by cord blood banks today.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of expanding hematopoietic stem cells (HSCs), comprising:
    (a) culturing an isolated population of HSCs with a composition comprising a cell culture medium that has been conditioned with Wharton's Jelly mesenchymal stem cells (WJSCs), wherein the cell culture medium does not include Wharton's Jelly stem cells (WJSCs), thereby producing a HSC culture; and
    (b) maintaining the HSC culture under conditions in which the HSCs expand in the culture, thereby expanding the HSCs.

2. The method of claim 1 wherein the cell culture medium is a basal medium.

3. The method of claim 1 wherein the cell culture medium is an enriched medium.

4. The method of claim 3 wherein the enriched medium comprises one or more cytokines that support growth of HSCs.

5. The method of claim 1 wherein the cell culture medium conditioned with WJSCs is obtained by culturing WJSCs in the medium for about 12 hours to about 48 hours.

6. The method of claim 1 wherein the conditions in which the HSCs expand in culture comprise maintaining the HSC culture at 37° C. in 5% $CO_2$.

7. The method of claim 1 wherein the HSCs are cultured for about 1 day, 5 days, 10 days or about 14 days.

8. The method of claim 1 wherein the HSCs are obtained from bone marrow, cord blood, peripheral blood, or a combination thereof.

9. The method of claim 1 wherein the HSCs and the WJSCs are obtained from different individuals.

10. The method of claim 1 wherein the HSCs and WJSCs are obtained from the same individual.

11. The method of claim 1 wherein the HSCs are human HSCs.

12. The method of claim 1 wherein the WJSCs are human WJSCs.

13. The method of claim 1 wherein the HSCs are expanded to about 10-fold or to about 25-fold compared to a suitable control.

14. The method of claim 1 further comprising separating the expanded HSCs from the culture medium that has been conditioned with the WJSCs, thereby obtaining isolated HSCs.

15. The method of claim 14 further comprising storing the isolated HSCs.

16. The method of claim 1 further comprising transplanting an effective amount of the expanded hematopoietic stem cells into an individual in need thereof.

17. The method of claim 16 wherein the individual has a malignant hematopoietic disease.

18. The method of claim 16 wherein the individual has a non-malignant hematopoietic disease.

19. The method of claim 1, wherein the HSCs are fetal liver HSCs.

20. A method of transplanting hematopoietic stem cells (HSCs) in an individual in need thereof, comprising:
- expanding an isolated population of HSCs ex vivo comprising culturing the HSCs with a composition comprising a cell culture medium that has been conditioned with Wharton's Jelly mesenchymal stem cells (WJSCs), wherein the cell culture medium does not include Wharton's Jelly stem cells (WJSCs), thereby producing a HSC culture;
- maintaining the HSC culture under conditions in which the HSCs expand in the culture, thereby expanding the HSCs and producing expanded HSCs; and
- introducing the expanded HSCs into the individual in need thereof, thereby transplanting HSCs in the individual.

21. The method of claim 20 wherein the expanded HSCs are the individual's own HSCs.

22. The method of claim 20 wherein the individual has a malignant hematopoietic disease.

23. The method of claim 20 wherein the individual has a non-malignant hematopoietic disease.

24. The method of claim 20 wherein the cell culture medium is a basal medium.

25. The method of claim 20 wherein the cell culture medium is an enriched medium.

26. The method of claim 25 wherein the enriched medium comprises one or more cytokines that support growth of HSCs.

27. The method of claim 20 wherein the cell culture medium conditioned with WJSCs is obtained by culturing WJSCs in the medium for about 12 hours to about 48 hours.

28. The method of claim 20 wherein the conditions in which the HSCs expand in culture comprise maintaining the HSC culture at 37° C. in 5% $CO_2$.

29. The method of claim 20 wherein the HSCs are cultured for about 1 day, 5 days, 10 days or about 14 days.

30. The method of claim 20 wherein the HSCs are obtained from bone marrow, cord blood, peripheral blood, or a combination thereof.

31. The method of claim 20 wherein the HSCs and the WJSCs are obtained from different individuals.

32. The method of claim 20 wherein the HSCs and WJSCs are obtained from the same individual.

33. The method of claim 20 wherein the HSCs are human HSCs.

34. The method of claim 20 wherein the WJSCs are human WJSCs.

35. The method of claim 20 wherein the HSCs are expanded to about 10-fold or to about 25-fold compared to a suitable control.

36. The method of claim 20 further comprising separating the expanded HSCs from the culture medium that has been conditioned with the WJSCs, thereby obtaining isolated HSCs.

37. The method of claim 20 wherein the individual is a human.

38. The method of claim 20, wherein the HSCs are fetal liver HSCs.

39. A method of transplanting hematopoietic stem cells (HSCs) in an individual in need thereof, comprising:
- providing an expanded population of HSCs, wherein the HSCs were expanded by culturing an isolated population of HSCs with a composition comprising a cell culture medium that has been conditioned with Wharton's Jelly mesenchymal stem cells (WJSCs), and wherein the cell culture medium does not include Wharton's Jelly stem cells (WJSCs); and
- introducing the expanded HSCs into the individual in need thereof, thereby transplanting HSCs in the individual.

* * * * *